US009226763B2

(12) United States Patent
To et al.

(10) Patent No.: US 9,226,763 B2
(45) Date of Patent: Jan. 5, 2016

(54) BLADE DEBRIDER

(75) Inventors: John T. To, Newark, CA (US); Hiep Nguyen, Milpitas, CA (US)

(73) Assignee: Spine View, Inc., Fremont, CA (US)

( * ) Notice: Subject to any disclaimer, the term of this patent is extended or adjusted under 35 U.S.C. 154(b) by 164 days.

(21) Appl. No.: 12/762,235

(22) Filed: Apr. 16, 2010

(65) Prior Publication Data
US 2011/0190803 A1 Aug. 4, 2011

Related U.S. Application Data

(63) Continuation-in-part of application No. 12/753,788, filed on Apr. 2, 2010, now Pat. No. 9,168,047.

(60) Provisional application No. 61/170,569, filed on Apr. 17, 2009.

(51) Int. Cl.
A61B 17/32 (2006.01)
(52) U.S. Cl.
CPC ...................... A61B 17/32 (2013.01)
(58) Field of Classification Search
CPC ...................... A61B 17/32; A61B 2017/32004; A61B 2017/320056; A61B 2017/320072; A61B 2017/32008; A61B 2017/320096
USPC ................. 606/170, 171, 179, 180, 183, 79; 600/584
See application file for complete search history.

(56) References Cited

U.S. PATENT DOCUMENTS

| 4,573,448 | A | 3/1986 | Kambin |
| 5,571,106 | A * | 11/1996 | Coufal et al. .................. 606/80 |
| 6,217,509 | B1 | 4/2001 | Foley et al. |
| 7,108,705 | B2 | 9/2006 | Davison et al. |
| 7,273,468 | B2 | 9/2007 | Bedell |
| 2008/0208230 | A1 * | 8/2008 | Chin et al. .................. 606/167 |

OTHER PUBLICATIONS

International Search Report for international application No. PCT/US2010/031495.
Written Opinion of the International Searching Authority for international application No. PCT/US2010/031495.
International Preliminary Report on Patentability for international application No. PCT/US2010/031495.

* cited by examiner

Primary Examiner — Kathleen Holwerda
Assistant Examiner — Anh Dang
(74) Attorney, Agent, or Firm — Morrison & Foerster LLP; Ross M. Carothers

(57) ABSTRACT

Systems and methods for treating disc herniation or degeneration, disc degeneration, and vertebral body fracture include surgical and endoscopic access and removal of disc tissue. The tissue removal devices that may be used include rotatable blade devices having flow control surfaces that may be inserted into a vertebral disc and rotated to pulverize the disc material and facilitate its removal.

10 Claims, 38 Drawing Sheets

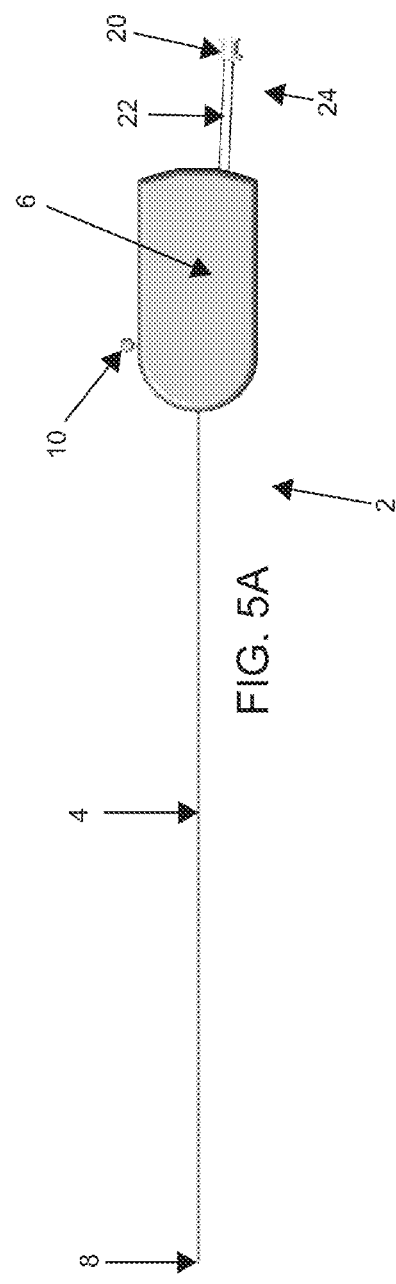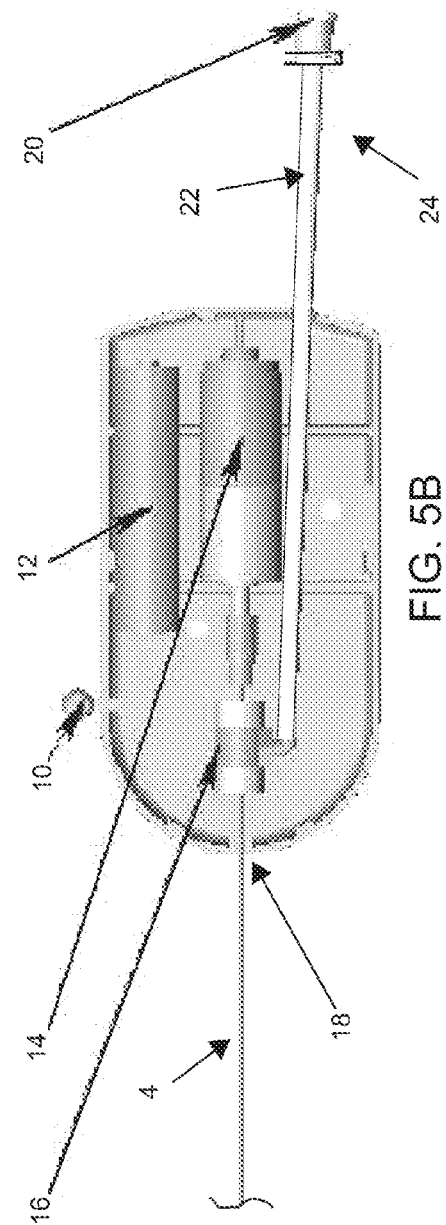

US 9,226,763 B2

BLADE DEBRIDER

CROSS-REFERENCE TO RELATED APPLICATIONS

The present application claims benefit under 35 U.S.C. §119(e) to U.S. Provisional Application No. 61/170,569, filed on Apr. 17, 2009, and is a continuation-in-part of U.S. application Ser. No. 12/753,788, filed on Apr. 2, 2010 now U.S. Pat. No. 9,168,047, all of which are hereby incorporated by reference in their entirety.

BACKGROUND

Vertebral disc herniation or degeneration are a common disorder where a portion of a vertebral disc, a cushion-like structure located between the bones of the spine, bulges out or extrudes beyond the usual margins of the disc and the spine. Disc herniation or degeneration are believed to be the result of a loss of elasticity of the tissue comprising the disc, and is associated with increasing age. Disc herniation or degeneration and other degenerative disc disease are also associated with spinal stenosis, a narrowing of the bony and ligamentous structures of the spine. Although disc herniation or degeneration can occur anywhere along the perimeter of the disc, it occurs more frequently in the posterior and posterior-lateral regions of the disc, where the spinal cord and spinal nerve roots reside. Compression of these neural structures can lead to pain, parasthesias, weakness, urine and fecal incontinence and other neurological symptoms that can substantially impact basic daily activities and quality of life.

Temporary relief of the pain associated with disc herniation or degeneration are often sought through conservative therapy, which includes positional therapy (e.g. sitting or bending forward to reduce pressure on spine), physical therapy, and drug therapy to reduce pain and inflammation. When conservative therapy fails to resolve a patient's symptoms, surgery may be considered to treat the structural source of the symptoms. Surgical treatments for disc herniation or degeneration traditionally involve open procedures that require extensive dissection of muscle, connective tissue and bone along a patient's back to achieve adequate surgical exposure. These surgeries also expose the patient to a significant risk of complications, due to the presence of critical neurovascular structures near the surgical site. For example, a discectomy procedure may be used to decompress the herniation by accessing the affected disc and removing a portion of the disc and any loose disc fragments. To achieve sufficient access to the affected disc, a portion of the lamina or bony arch of the vertebrae may be removed, thereby increasing the invasiveness of the procedure. When discectomy fails to resolve a patient's symptoms, more drastic measures may include disc replacement surgery or vertebral fusion.

BRIEF SUMMARY

Systems and methods for treating disc herniation or degeneration, disc degeneration, and vertebral body fracture include surgical and endoscopic access and removal of disc tissue. The tissue removal devices that may be used include rotatable blade devices having flow control surfaces that may be inserted into a vertebral disc and rotated to pulverize the disc material and facilitate its removal.

BRIEF DESCRIPTION OF THE DRAWINGS

FIG. 5A is a side elevational view of an embodiment of a tissue removal device; FIG. 5B is a detailed cutaway view of the device in FIG. 5A;

FIGS. 21A to 21B are various perspective views of the travel limiter. FIGS. 21C to 21F depict examples of how the travel limiter may be used with one example of a tissue-removal device.

DETAILED DESCRIPTION OF THE INVENTION

Figure 1:
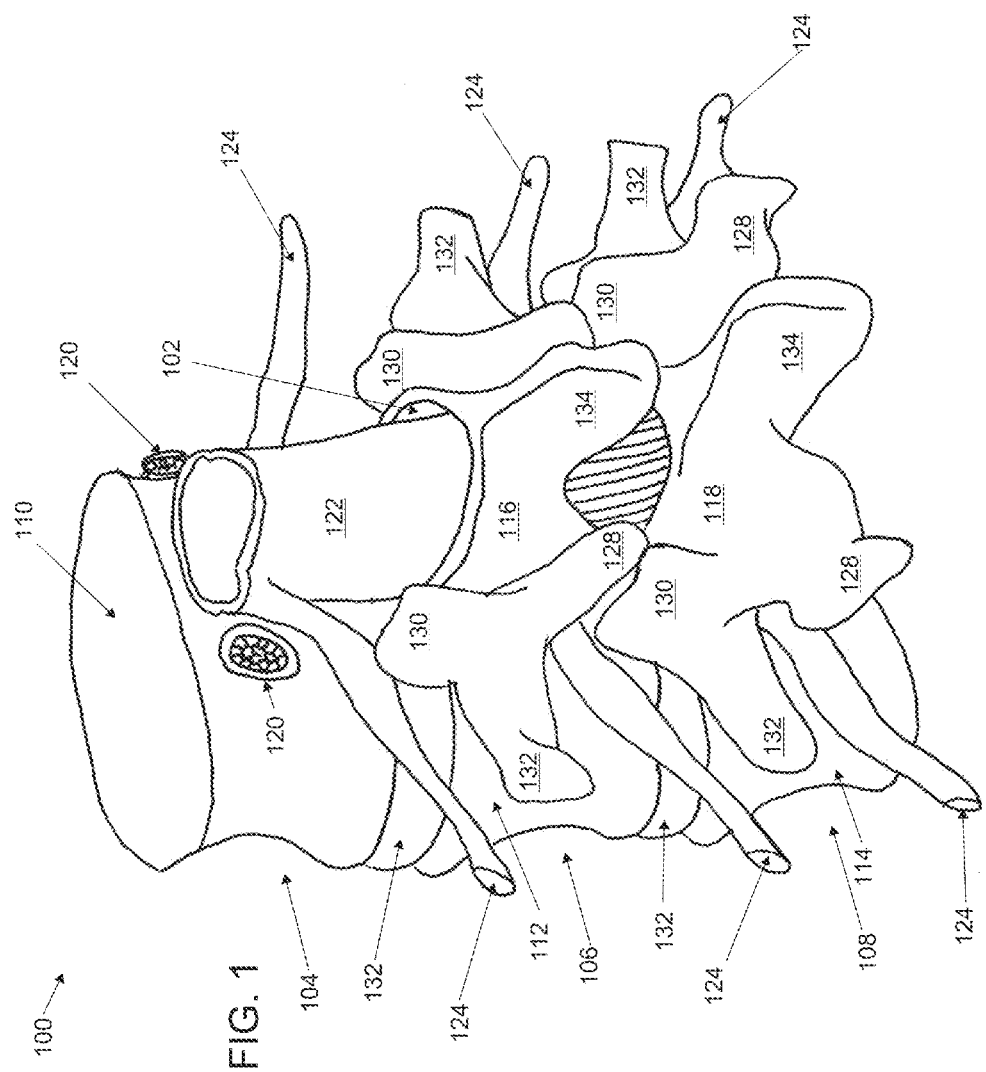
FIG. 1 is a schematic perspective view of a portion of a lumbar spine.
Figure 2:
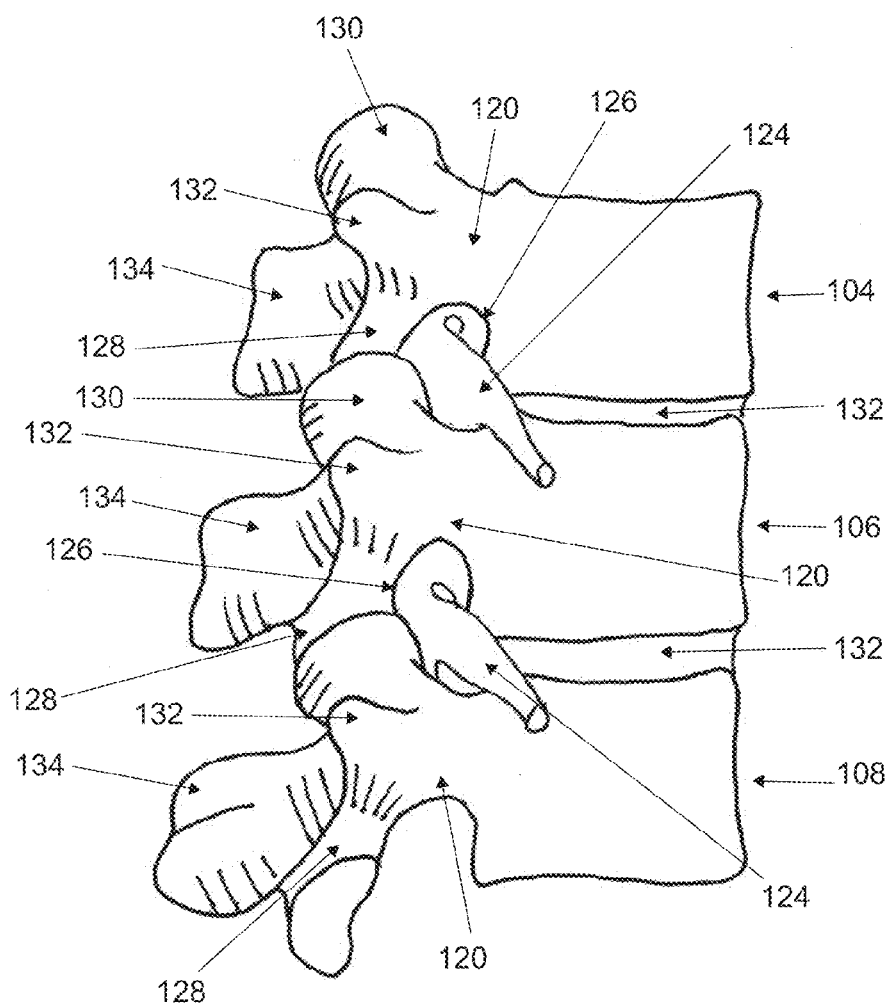
FIG. 2 is a schematic side elevational view of a portion of the lumbar spine.

FIGS. 1 and 2 are schematic views of a lumbar region of a spine 100. The vertebral canal 102 is formed by a plurality of vertebrae 104, 106, and 108, which comprise vertebral bodies 110, 112 and 114 anteriorly and vertebral arches 116 and 118 posteriorly. The vertebral arch and adjacent connective tissue of the superior vertebra 104 has been omitted in FIG. 1 to better illustrate the spinal cord 122 within the vertebral canal 102. Spinal nerves 124 branch from the spinal cord 122 bilaterally and exit the vertebral canal 102 through intervertebral foramina 126 (seen best in FIGS. 2 and 3) that are formed by the adjacent vertebra 104, 106 and 108. The intervertebral foramina 126 are typically bordered by the inferior surface of the pedicles 120, a portion of the vertebral bodies 104, 106 and 108, the inferior articular processes 128, and the superior articular processes 130 of the adjacent vertebrae. Also projecting from the vertebral arches 116 and 118 are the transverse processes 132 and the posterior spinous processes 134 of the vertebrae 106 and 108. Located between the vertebral bodies 110, 112 and 114 are the vertebral discs 123.

Figure 3:
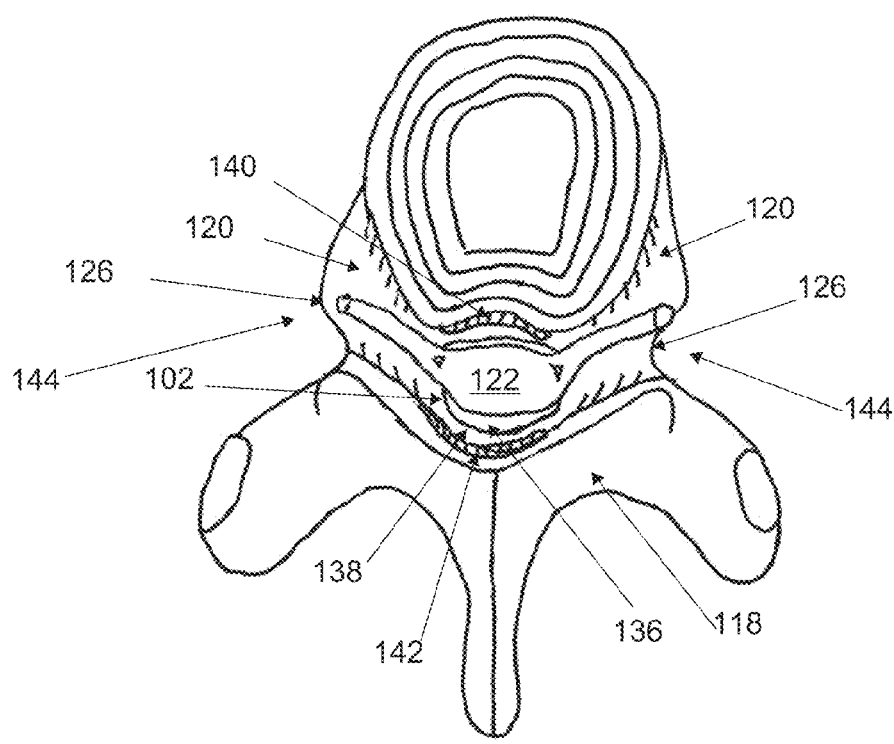
FIG. 3 is a schematic superior view of a portion of a lumbar vertebra and disc.

Referring to FIG. 3, the spinal cord 122 is covered by a thecal sac 136. The space between the thecal sac 136 and the borders of the vertebral canal 102 is known as the epidural space 138. The epidural space 138 is bound anteriorly and posteriorly by the longitudinal ligament 140 and the ligamentum flavum 142 of the vertebral canal 102, respectively, and laterally by the pedicles 120 of the vertebral arches 116 and 118 and the intervertebral foramina 126. The epidural space 138 is contiguous with the paravertebral space 144 via the intervertebral foramina 126.

Figure 4A:
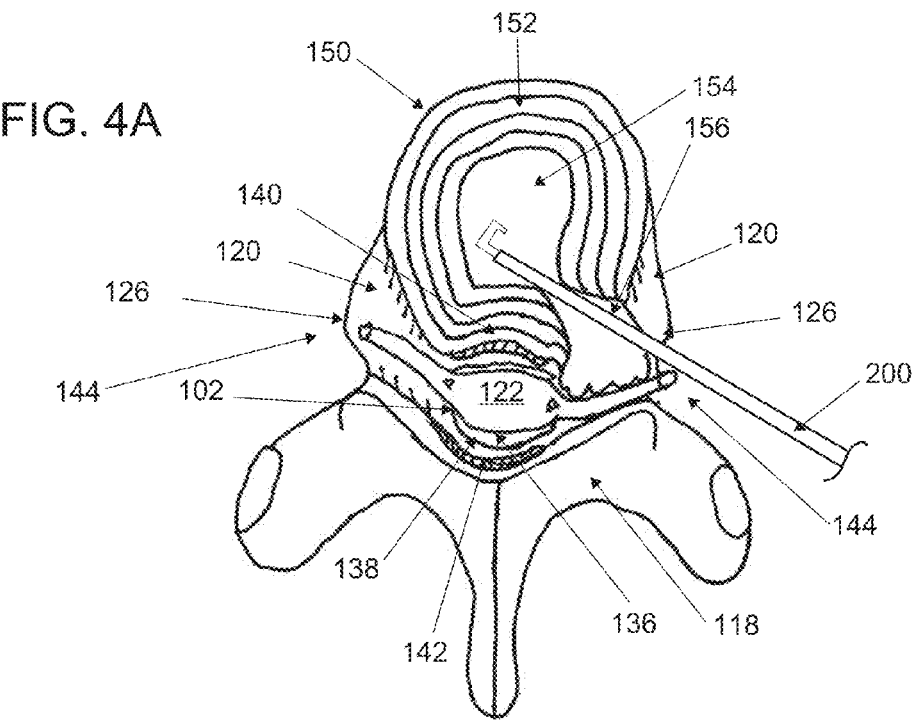
FIGS. 4A and 4B are schematic superior views of a herniated disc during and after treatment, respectively.

Referring to FIG. 4A, a vertebral disc 150 typically comprises an outer, multi-layer, annular band of connective tissue, known as the annulus fibrosus 152, which encases a gel-like resilient material known as the nucleus pulposus 154. The nucleus pulposus 154 acts as a shock-absorbing structure for the forces acting on the spine. Both the annulus fibrosus 152 and the nucleus pulposus 154 are elastic collagenous structures which, over time, may decrease in elasticity and cause the nucleus pulposus to bulge out at a weakened region of the annulus fibrosus 152, and even extrude through the annulus fibrosus 152. FIG. 4A schematically depicts an extrusion 156 of the nucleus pulposus 154, which has penetrated through the wall of the annulus fibrosus 152 within an intervertebral foramen 126 and compressed a nerve 124 exiting the spine. Although the extrusion 156 remains in continuity with the remaining nucleus pulposus 154, the extrusion 156 may sometimes pinch off or separate, resulting in the sequestration of a portion of the nucleus.

Figure 4B:
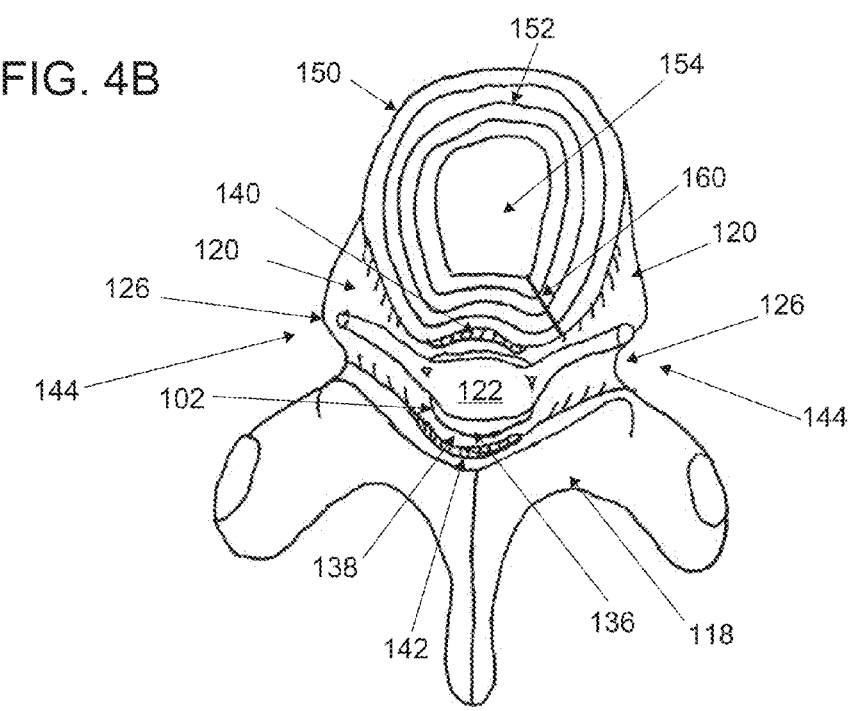

As mentioned previously, treatments of disc herniation or degeneration may involve internal access to the affected disc with removal or volume reduction of the disc material. This may relieve the pressure causing the bulging or extrusion to at least partially restore the profile of the disc. In FIG. 4A, for example, a tissue removal device 200 has been inserted into the extrusion 156 extending out of the herniated disc 150. The tissue removal device 200 is then actuated to break up and remove the extruded material. In some embodiments, the tissue removal device 200 may be further inserted distally into the disc 150. Additional tissue with the disc 150 may then be removed. As shown in FIG. 4B, after removing a volume of the nucleus pulposus 154 and relieving some of the pressure causing the extrusion 156, the extrusion 156 was able to retract back into the disc 150, thereby reducing the extrusion pathway 160 and relieving compression of the spinal nerve 124. Although contralateral access of the herniated disc is depicted in FIG. 4A, ipsilateral access may also be used. Furthermore, direct tissue removal of the extruded herniated disc may also be performed. In other examples, the tissue removal device 200 may be used to perform discectomy to prepare the disc space for an interbody fusion procedure, which may be performed as an open surgery.

Devices used to remove disc tissue for discectomy or nucleotomy may include lasers, discectomes, trephines, burrs, rongeurs, rasps, curettes and cutting forceps. The tissue removal device may be used for any of a variety of procedures, including but not limited to discectomy, nucleotomy, lysis of adhesions, and other tissue removal procedures in the spine and throughout other regions of the body. FIG. 5A depicts one embodiment of a tissue removal device 2, comprising an outer tube 4 coupled to a housing 6. The static outer tube 4 covers a rotating drive shaft (not shown) that is attached to a tissue removal assembly 8. In other embodiments, the tissue removal device 2 may lack an outer tube and the drive shaft of the tissue removal device may be inserted into a lumen of a cannula or other access device. The housing 6 contains one or more components configured to control the tissue removal assembly 8 and other optional features of the tissue removal device 2. The tissue removal assembly 8, examples of which are described in greater detail below, may be configured to cut, chop, grind, burr, pulverize, debride, debulk, emulsify, disrupt or otherwise remove tissue when rotated at various speeds. Emulsification includes, for example, forming a suspension of tissue particles in a medium, which may be the existing liquid at the target site, liquid added through the tissue removal device, and/or liquid generated by the debulking of the tissue. Optional components may include, but are not limited to, a motor configured to rotate or move the tissue removal assembly, a power source or power interface, a motor controller, a tissue transport assembly, an energy delivery or cryotherapy assembly, a therapeutic agent delivery assembly, a light source, and one or more fluid seals. The optional tissue transport assembly may comprise a suction assembly and/or a mechanical aspiration assembly. One or more of these components may act through the outer tube 4 to manipulate the tissue removal assembly and/or other components located distal to the housing 6, or from the housing 6 directly. For example, the tissue removal device 2 further comprises an optional port 20 that may be attached to an aspiration or suction source to facilitate transport of tissue or fluid out of the target site or patient. The suction source may be a powered vacuum pump, a wall suction outlet, or a syringe, for example.

The housing 6 may further comprise a control interface 10 that may be used to control the power state of the tissue removal device 2, including but not limited to on and off states. In this particular embodiment, the control interface 10 comprises a lever or pivot member, but in other embodiments, control interface 10 may comprise a push button, a slide, a dial or knob. In some embodiments, the control interface 10 may also change the motor speed and/or movement direction of the tissue removal assembly 8. A bi-directional tissue removal device may be provided, for example, as a potential safety feature should the tissue removal assembly 8 get lodged in a body tissue or structure. The web-like connective tissue that may be found in the epidural space may get wound onto or caught up on the burr device or other tissue removal device. This connective tissue may be dislodged with a bi-directional tissue removal device by reversing the direction of rotation to unwind the tissue. The control interface 10 may be analog or digital, and may comprise one or more detent positions to facilitate selection of one or more pre-selected settings. In other embodiments, a separate motor control interface may be provided for one or more features of the motor. In still other embodiments, control interfaces for other features of the tissue removal device may be provided.

Referring now to FIG. 5B, the tissue removal device 2 in FIG. 5A is illustrated with a portion of the housing 6 removed to show various internal components. In this embodiment, the tissue removal device 2 further comprises a battery 12 to provide power to the motor 14 which drives the tissue removal assembly 8. In other embodiments, a connector to an external power source may be provided in addition to, or in lieu of, the battery 12. The type of battery and power provided may differ depending upon the particular power needs of the motor and/or other components of the tissue removal device 2.

In some embodiments, the motor 14 of the tissue removal device 2 is a DC motor, but in other embodiments, the motor 14 may have any of a variety of configurations, including but not limited to an AC or a universal motor. The motor 14 may be a torque, brushed, brushless or coreless type of motor. In some embodiments, the motor 14 may be configured to provide a rotational speed of about 500 rpm to about 200,000 rpm or more, sometimes about 1,000 rpm to about 40,000 rpm, and at other times about 5,000 rpm to about 20,000 rpm. The motor 14 may act on the tissue removal assembly 8 via the outer tube 4, or a by drive member located within the outer tube 4. In some further embodiments, a fluid seal 16 may be used to protect the motor 14 and/or other components of the housing 6 from any fluids or other materials that may be transported through the outer tube 4, or through the housing aperture 18. In some embodiments, a connector or seal may be provided about the housing aperture 18 to permit coupling of the housing 6 to a trocar, an introducer, a cannula or other tubular member into which the tissue removal assembly 8 and the outer tube 4 are inserted. In some embodiments, the tissue removal device may be used with an introducer or cannula having an outer diameter of about 0.01 cm to about 1.5 cm or more, sometimes about 0.1 cm to about 1 cm, and other times about 1.5 mm to about 6 mm.

As shown in FIGS. 5A and 5B, the tissue removal device 2 may further comprise a conduit 24 which may be used to connect the tissue removal device 2 and an aspiration or suction source. An aspiration or suction source may be used, for example, to transport fluid or material through a lumen or conduit of the outer tube 4 or through a tubular member in which the outer tube 4 is inserted. In one particular embodiment, the conduit 24 comprises a port 20 which communicates with the fluid seal 16 via a length of tubing 22. The fluid seal 16 is configured to permit flow of fluid or material between the outer tube 4 and the tubing 22, while permitting movement of the outer tube 4 or a drive member therein coupled to the motor 14. In other embodiments, the conduit 24 may further comprise additional components, including but not limited to a fluid or material trap, which may be located within or attached to the housing 6, or attached to the port 20 or the tubing 22, or located anywhere else along the pathway from the tissue removal assembly 8 to the suction source. In some embodiments, a separate port may be provided for infusing or injecting substances into target site using the tissue removal device 2. In other embodiments, the conduit 24 may be used for both withdrawal and infusion of materials and/or fluids, or for infusion only. Depending upon the configuration of the tissue removal device, withdrawal and/or infusion may occur at the distal end of the outer tube 4, and/or through one or more openings of the tissue removal assembly 8. In other embodiments, a port may be used to insert a coagulation catheter, an ablation catheter or other energy delivery device to the target site.

In some embodiments, the outer tube comprises an outer tubular member with at least one lumen, and an elongate drive member configured to mechanically couple the motor to the tissue removal assembly. In other embodiments, the outer tube may contain additional members, for example, to adjust or control the configuration of the tissue removal assembly. In some embodiments, the outer tube 4 may comprise one or more lumens containing control wires, which may be used to manipulate the deflections of the distal end of the outer tube. The outer tube and optional drive members may be rigid or flexible. The outer tube may be pre-shaped with a linear or a non-linear configuration. In some embodiments, the outer tube and the components is configured to be user-deformable, which may facilitate access to particular target sites, or may be user-steerable using a steering mechanism comprising one or more pull wires or tension elements. In some embodiments, a stiffening wire or element may be inserted into the outer tube to provide additional stiffness to the tissue removal device. The length of the outer tube between the tissue removal element and the motor or housing may vary from about 0 cm to about 30 cm or more in some embodiments, sometimes about 4 cm to about 20 cm, and other times about 10 cm to about 14 cm.

In other embodiments, the tissue removal device may comprise a tissue removal assembly that may be detachably attachable to the shaft of a motor or coupled to a motor. In still other embodiments, the tissue removal device may comprise a tissue removal assembly coupled to a shaft, wherein the shaft may be detachably attachable to a motor or a shaft coupled to a motor.

In some embodiments, the housing 6 is configured with a size and/or shape that permits handheld use of the tissue removal device 2. In other embodiments, the tissue removal device 2 may comprise a grip or structure located about the outer tube 4 to facilitate handling by the user, while the proximal end of the outer tube 4 is attached to a benchtop or cart-based machine, for example, or a mounted or fixed machine. In these embodiments, the grip may or may not contain any other components of the tissue removal device, such as a motor, while the machinery at the proximal end of the outer tube 4 may contain one or more other components, such as a suction system or various radiofrequency ablation components, for example. In some embodiments, the housing 6 may have a length of about 1 cm to about 12 cm or more, sometimes about 2 cm to about 8 cm, and other times about 3 cm to about 5 cm. The average diameter of the housing (or other transverse dimension to the longitudinal axis of the housing) may be about 1 cm to about 6 cm or more, sometimes about 2 cm to about 3 cm, and other times about 1.5 cm to about 2.5 cm. The housing 6 may further comprise one or more ridges, recesses or sections of textured or frictional surfaces, including but not limited to styrenic block copolymers or other polymer surfaces.

Figure 6:
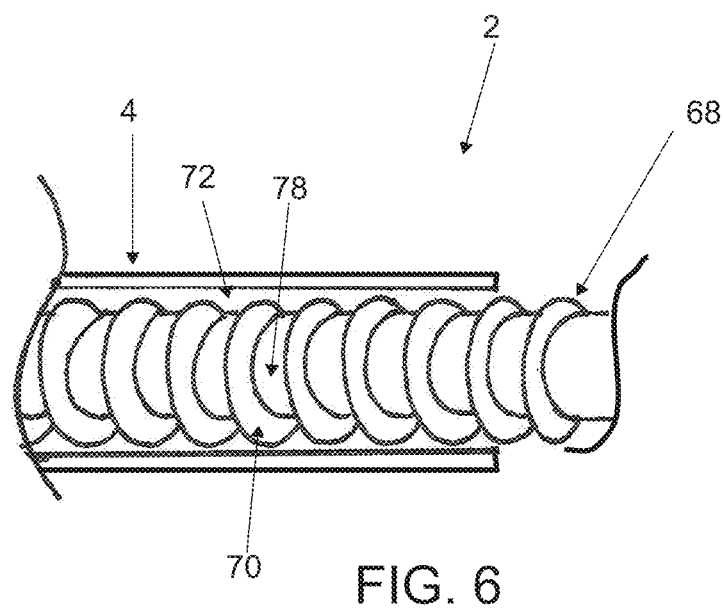
FIG. 6 is a detailed view of one embodiment of an optional tissue transport mechanism.

As illustrated in FIG. 6, a tissue removal device may optionally comprise a tissue transport assembly 68, which may be used to facilitate transport or removal of tissue within or along the outer tube 4. In the particular embodiment depicted, the tissue transport assembly 68 comprises a helical member 70 mounted on a drive member 78 that may be rotated. Actuation of the drive member 78 may mechanically facilitate proximal movement of tissue or other materials within the channel or the lumen 72 of the outer tube 4 by rotating the helical member 70. The actuated drive member 78 will also rotate the distal burr element or other tissue removal assembly 8. In some embodiments, use of the tissue transport assembly 68 may be performed at lower rotational speeds when tissue debulking is not concomitantly performed. When rotated in the opposite direction, the helical member 70 may be used expel or distally transport tissue, fluid or other materials or agents from the outer tube 4 or supplied to an infusion port of the housing 6.

In some embodiments, the helical member 70 may have a longitudinal dimension of about 2 mm to about 10 cm or more, sometimes about 3 mm to about 6 cm, and other times about 4 mm to about 1 cm. In other embodiments, the longitudinal dimension of the helical member 70 may be characterized as a percentage of the longitudinal dimension of the outer tube 4, and may range from about 5% to about 100% of the longitudinal dimension of outer tube 4, sometimes about 10% to about 50%, and other times about 15% to about 25%, and still other times is about 5% to about 15%. Although the helical member 70 depicted in FIG. 6 rotates at the same rate as the tissue removal assembly, due to their mounting or coupling onto common structure, drive member 78, in other embodiments, the helical member may also be configured to rotate separately from drive member. For example, a helical member may comprise a helical coil located along at least a proximal portion of the lumen of the outer tube but is not mounted on the drive member. In this particular example, the helical member may rotate independently of the drive member. In still other embodiments, the helical member 70 may be mounted on the surface of the lumen 72 and can be used to transport tissue or substances along the lumen 72 by rotation of the outer tube 4, independent of the drive member 78 or a tissue removal assembly.

Although the helical member 70 is depicted as a continuous structure, in some embodiments, the helical member 70 may be interrupted at one or more locations. Also, the degree or angle of tightness of the helical member 70 may vary, from about 0.5 turns/mm to about 2 turns/mm, sometimes about 0.75 turns/mm to about 1.5 turns/mm, and other times about 1 turn/mm to about 1.3 turns/mm. The cross-sectional shape of the helical member 70 may be generally rounded as depicted in FIG. 6, but in other embodiments, may have one or more edges. The general cross-sectional shape of the helical member 70 may be circular, elliptical, triangular, trapezoidal, squared, rectangular or any other shape. The turn tightness and cross-sectional shape or area of the helical member 70 may be uniform or may vary along its length. In some embodiments, multiple the helical members 70 may be provided in parallel or serially within the outer tube 4.

In some embodiments, the drive member 78 may be configured to extend distally and retract from the outer tube 4 by a length of about 0.01 cm to about 2 cm or more, sometimes about 0.02 cm to about 1.5 cm and other times about 0.05 to about 1 cm. In some embodiments, the helical member 70 is located proximal to the tissue removal assembly at a distance of about 0.01 cm to about 2 cm or more, sometimes about 0.02 cm to about 1.5 cm and other times about 0.05 to about 1 cm. In some embodiments, when drive member 78 is maximally extended from outer tube 4, helical member 70 may protrude from outer tube 4 by a longitudinal dimension of about 0.01 cm to about 2 cm or more, sometimes about 0.1 cm to about 1 cm, and other times about 0.25 cm to about 0.5 cm. In some embodiments, the degree of extension of the drive member 78 and/or the helical member 70 may affect the degree of tissue transport by the tissue transport assembly.

Figure 7A:
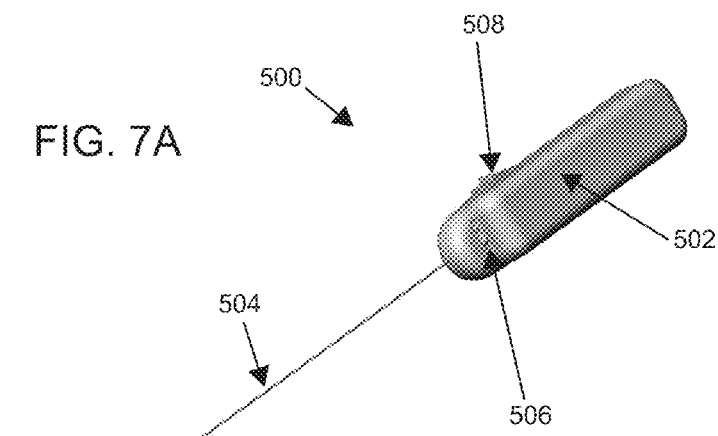
FIGS. 7A and 7B are perspective and side elevational views of another embodiment of a tissue removal device.
Figure 7B:
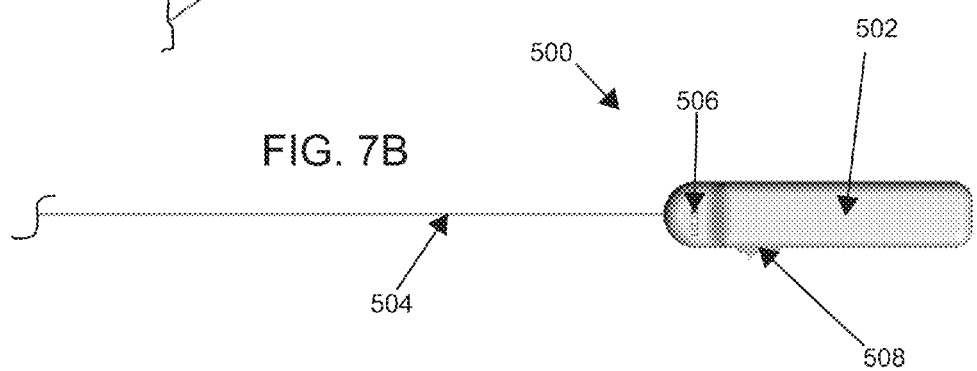

Referring to FIGS. 7A and 7B, in another embodiment, a tissue removal device 500 comprises a housing 502 and an outer shaft 504. The housing 502 may include an adjustment mechanism with a thumbwheel 506 configured to adjust the retraction and extension of extendable tissue removal assembly (not shown). The thumbwheel 506 may provide a continuous range of change to extendable tissue removal assembly, but in other embodiments, the turning of thumbwheel 506 may be configured with clicks or detents that provide one or more preset positions. As mentioned previously, any of a variety of other control mechanisms and interfaces may be used. The adjustment mechanism may comprise one or more blocking elements or other adjustment limiting configurations to resist or prevent overextension of extendable tissue removal assembly. For example, limit structures may be provided in housing 502 to resist overextension of extendable tissue removal assembly (not shown). In this particular embodiment, tissue removal device 500 is configured to rotate the tissue removal assembly at a fixed rotational speed, controllable by a rocker-type power switch 508. As mentioned previously, however, any of a variety of power and/or speed control mechanisms may be used.

Figure 7C:
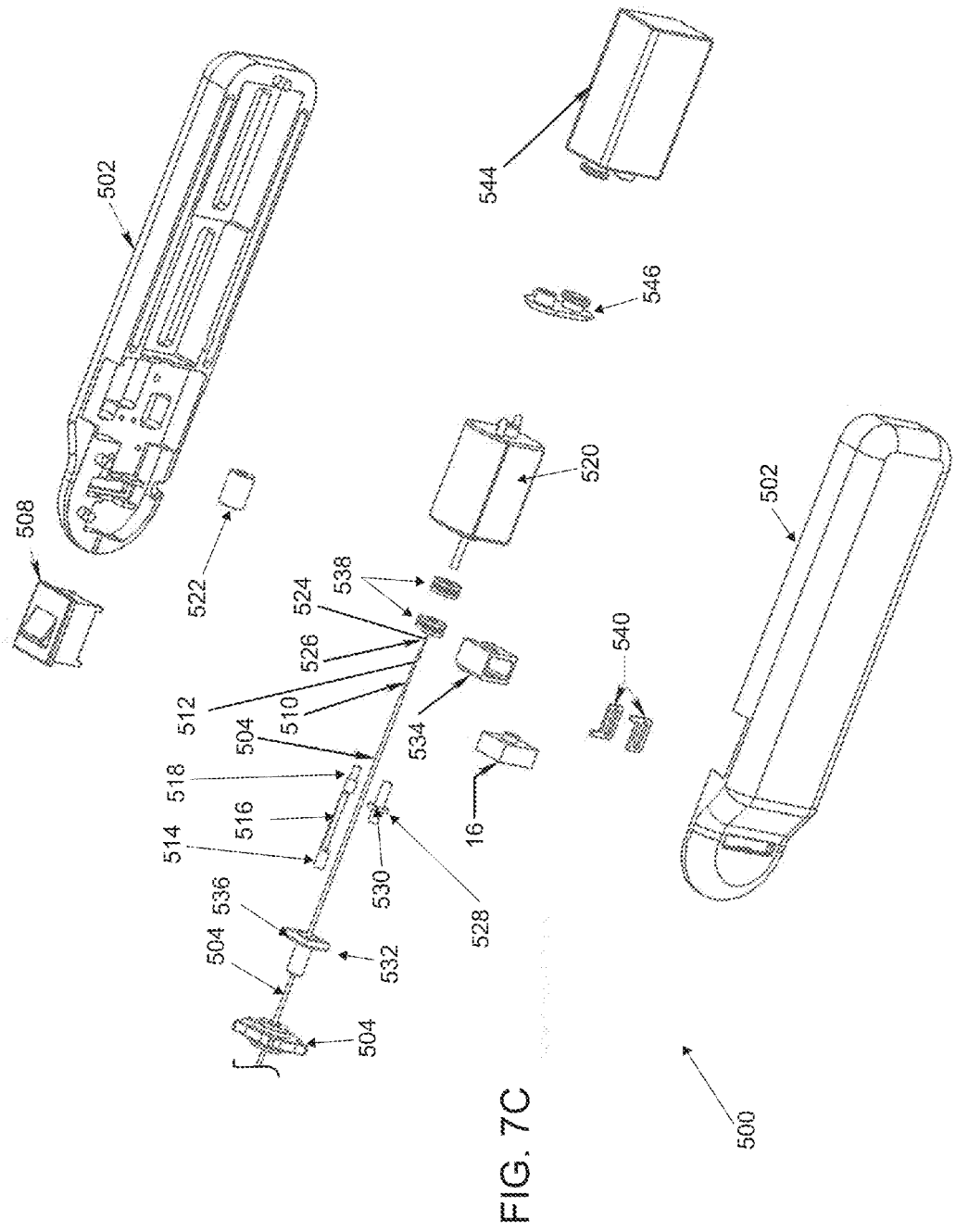
FIG. 7C is a component view of the tissue removal device in FIGS. 7A and 7B.
Figure 7D:
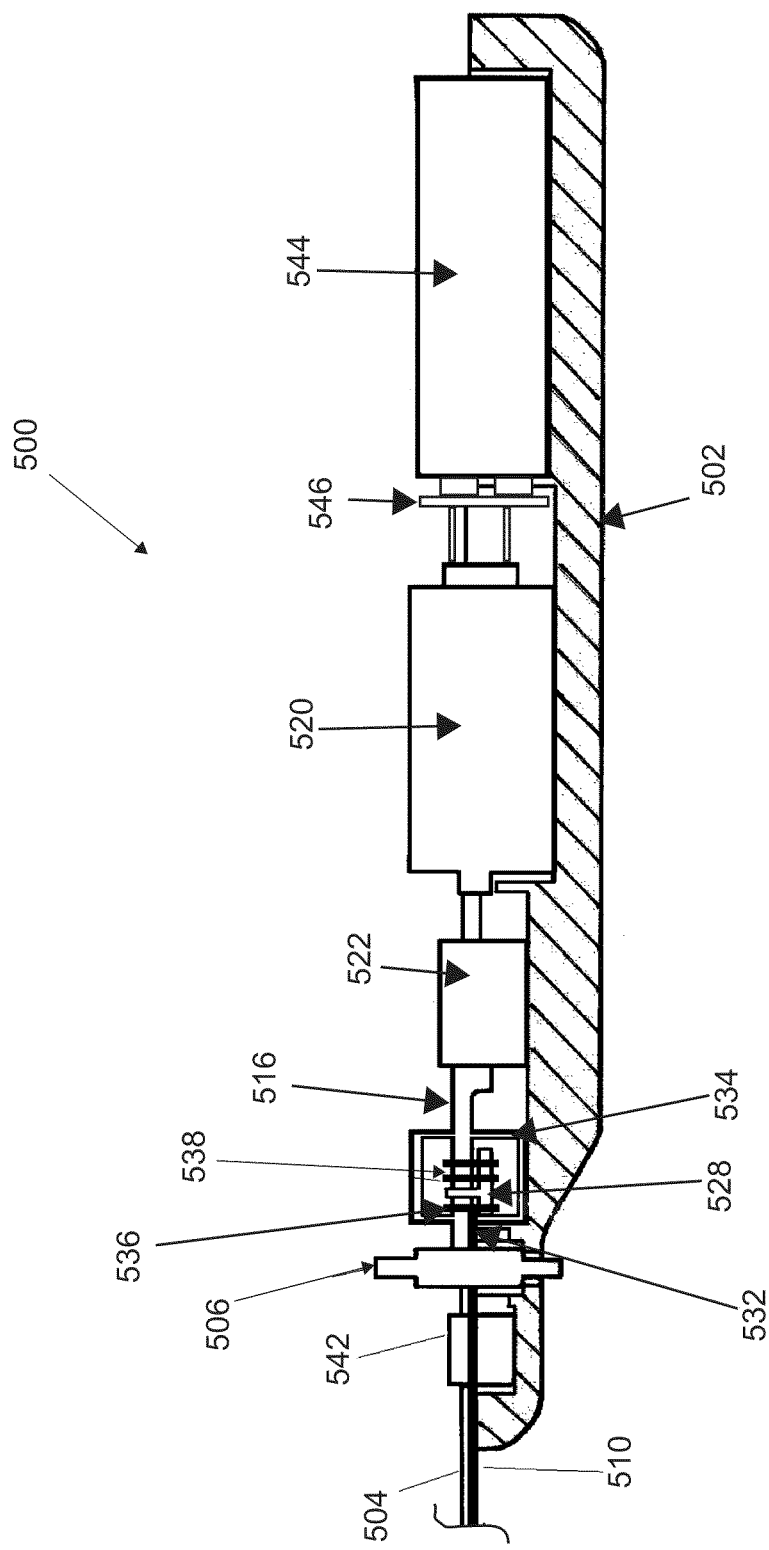
FIG. 7D is a cross-sectional view of the tissue removal device in 7A and 7B with a portion of the housing removed.
Figure 8A:
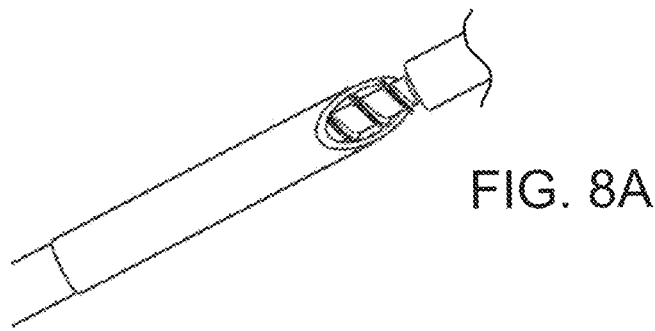
FIG. 8A depicts the distal end of another embodiment of a tissue removal device with a blunt tip and in an extended configuration.
Figure 8B:
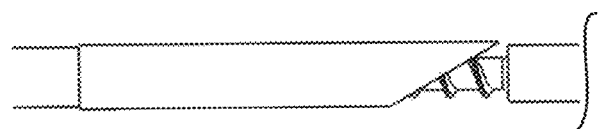
FIGS. 8B to 8D depict various views of the tissue removal device in FIG. 8A in the retracted configuration.
Figure 8C:
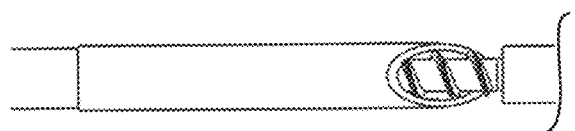
Figure 8D:
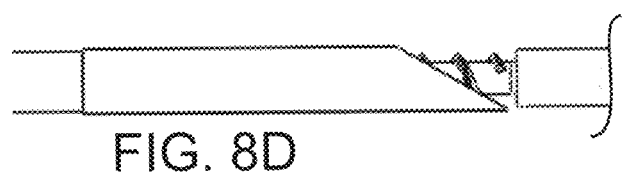

Referring to FIGS. 7C and 7D, FIG. 7C is a component view of the internal components within housing 502, while FIG. 7D is a schematic cross-sectional view of the internal components with a portion of housing 502 removed. As shown in FIG. 7C, a drive member 510 rotatably resides within the outer shaft 504 of the tissue removal device 500. The distal end (not shown) of the drive member 510 is coupled to the tissue removal assembly (not shown), while the proximal end 512 of the drive member 510 is coupled to the distal end 514 of a driveshaft 516. The proximal end 518 of the driveshaft 516 may be coupled to a motor 520, either directly or through a coupler 522. The coupler 522 may be configured to permit some axial movement of driveshaft 526. The proximal end 524 of an adjustment member 526 protrudes from the proximal end 510 of drive member 512 and is attached to a drive key 528. The drive key 528 may comprise a flange 530 that is slidably located between the proximal and distal ends 518 and 514 of the driveshaft 516. The thumbwheel 506 may be movably coupled to a thrust member 532 so that the rotation of the thumbwheel 506 results in the axial movement of thrust member 532. In some embodiments, the thrust member 532 may be configured with helical threads that are complementary to a threaded lumen of the thumbwheel 506. In other embodiments, however, the thrust member may comprise a slide member, a pivot member or other coupling structure. The thrust member 532 may be configured to axially slide the drive key 528 through a retaining structure 534 which movably couples the thrust member 532 to the drive key 528. The retaining structure 534 permits the rotation of the driveshaft 516 by the motor 520 while also coupling the axial movements of the thrust member 532 to the drive key 528, thereby permitting adjustment of the tissue removal assembly located at the distal end of the shaft 504 while maintaining the ability of the drive member 510 to rotate. The thrust member 532 may comprise a flange 536 to facilitate retention of the thrust member 532 within the retaining structure 534. The flange 536 may comprise one or more bearings to facilitate rotational movement of the drive key 528 against the non-rotating flange 536. The retaining structure 534 may also contain one or more retaining bearings 538 to facilitate the rotation of the driveshaft 516 against the drive key 528 while transmitting any axial forces to the drive key 528. The retaining structure 534 is optionally provided with one or more limiters 540, which may be used to restrict overextension or retraction of the tissue removal assembly. A seal 542 may be provided around the outer shaft 504 to protect the contents of the housing 502. Other examples of drive shafts couplings and adjustment mechanisms that may be used are disclosed in U.S. Pat. No. 5,030,201, which is hereby incorporated by reference in its entirety.

Figure 18A:
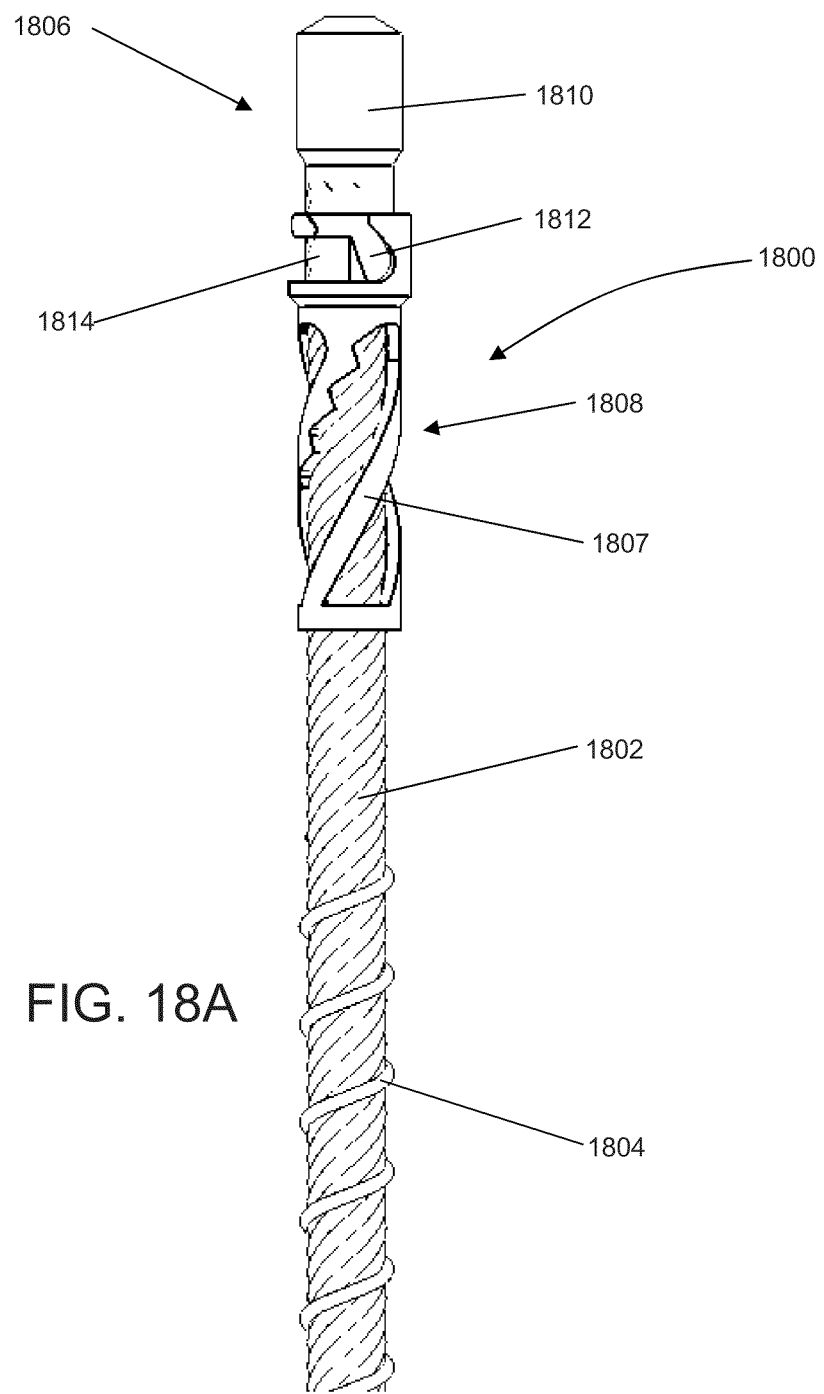
FIG. 18A illustrates an embodiment of tissue transport assembly that may be used with a tissue-removal assembly.
Figure 18B:
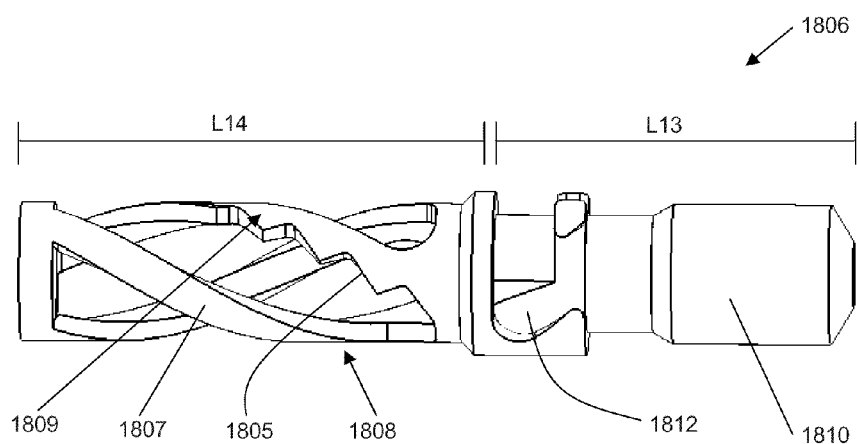
FIGS. 18B to 18I illustrate various examples of impellers that may be used in a tissue transport assembly.
Figure 18C:
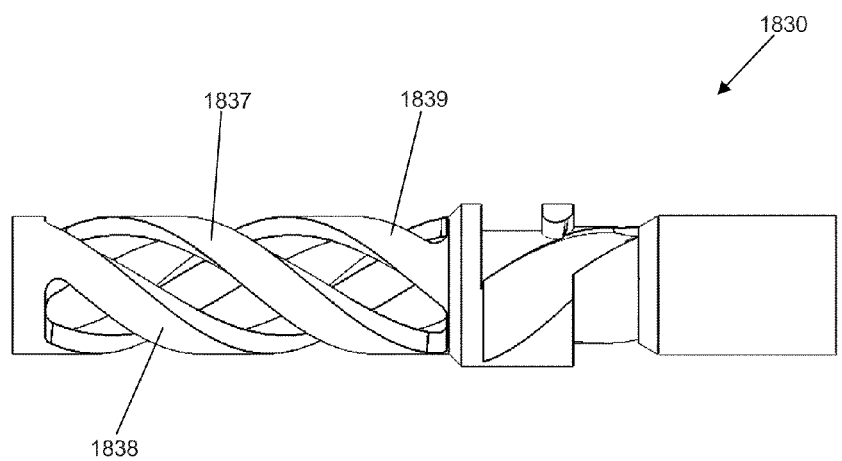

As illustrated in FIG. 7D, the tissue removal device 500 may be powered using a battery 544 that is coupled to the motor 520 using a battery connector 546. As depicted in FIG. 18C, battery 544 may be a standardized battery, such as a 9-volt battery, but may also be a customized battery. In still other examples, the tissue removal device may comprise a power source connector to permit utilization of an external power source. The power source connector may be in lieu of or in addition to a battery power source.

FIGS. 8A to 8D further depict an optional feature of the tissue removal system comprising an outer tubular shaft 718 with a cutting edge 720. In this particular example, the cutting edge 720 is a beveled edge, which may or may not be at least partially sharpened. In other examples, the cutting edge may be sharpened but not beveled. As further depicted in FIGS. 8A to 8D, the inner shaft 722 located in the outer tubular shaft 718 may comprise at least one optional thread structure 724 which is configured to draw fluids and/or other materials into the outer tubular shaft 718 for removal from the target site. A beveled or sharpened edge may further shear or break-up materials pulled into the outer tubular shaft 718 by the thread structure 724. In some examples, the rotational sense of the thread structure 724 may be the same as the distal tissue removal element, but in other examples, the thread structure 724 and the distal tissue removal element may be opposite rotational senses.

Figure 9:
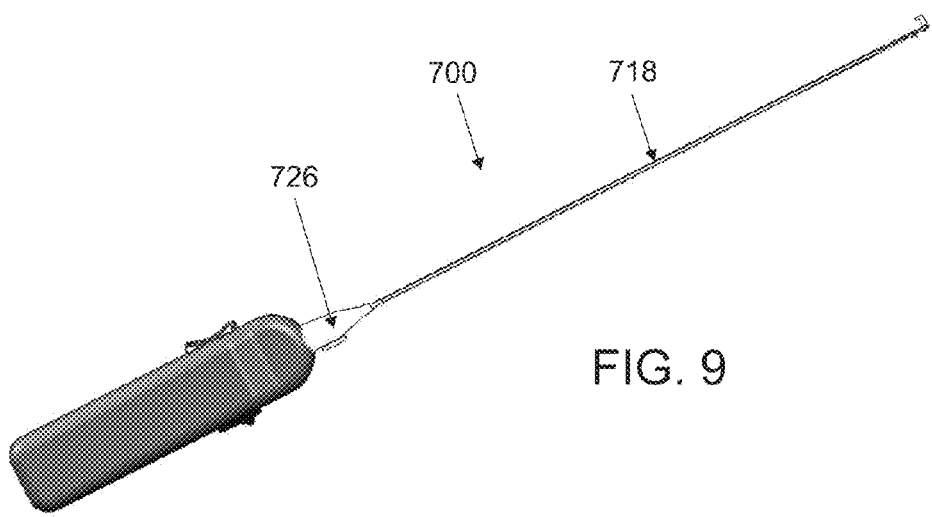
FIG. 9 illustrates the tissue removal device of FIG. 8A with an optional viewing chamber.

FIG. 9 depicts another optional feature of a tissue removal system 700, comprising an optically transparent chamber 726. Although the optically transparent chamber section 726 in FIG. 9 is located distally at the attachment of the outer tubular shaft 718, in other examples, the optically transparent housing chamber 726 may be located at a more proximal location. The optically transparent housing section 726 comprises an optically clear passageway or cavity in communication with the lumen of the outer tubular shaft 718 so that any fluid and/or materials either injected distally or removed proximally may be viewed by the user. In some instances, the passageway or cavity may have a volume of at least about 0.5 cc, sometimes about 1 cc, and other times about 2 cc or more. The optically transparent housing chamber 726 may also comprise markings to identify the volume of material that has aspirated or prepared for infusion or irrigation, for example. The optically transparent chamber 726 may also features a removable cap to empty the contents for of the chamber 726, to reduce clogging or to collect a diagnostic tissue sample. In some examples, the tissue removal system may have one or more infusion lumens with one or more openings at the base, rotatable shaft, and/or distal tip of the tissue removal system, which may be used in addition to or in lieu distal end of the outer tubular shaft 718. In other examples, the tissue removal system may be removed from the vertebral body and a separate infusion instrument may be used to deliver therapeutic agents or materials.

Figure 10A:
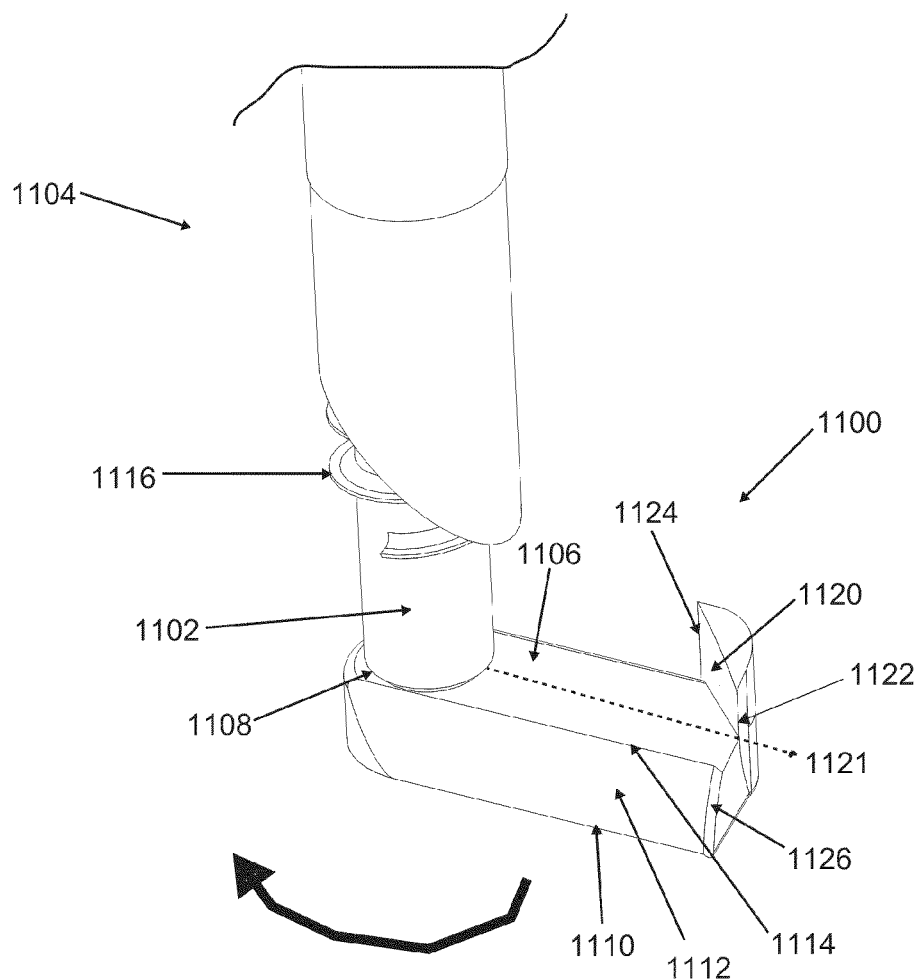
FIG. 10A is a perspective view of a distal end of a tissue removal device with a rotatable blade element.
Figure 10B:
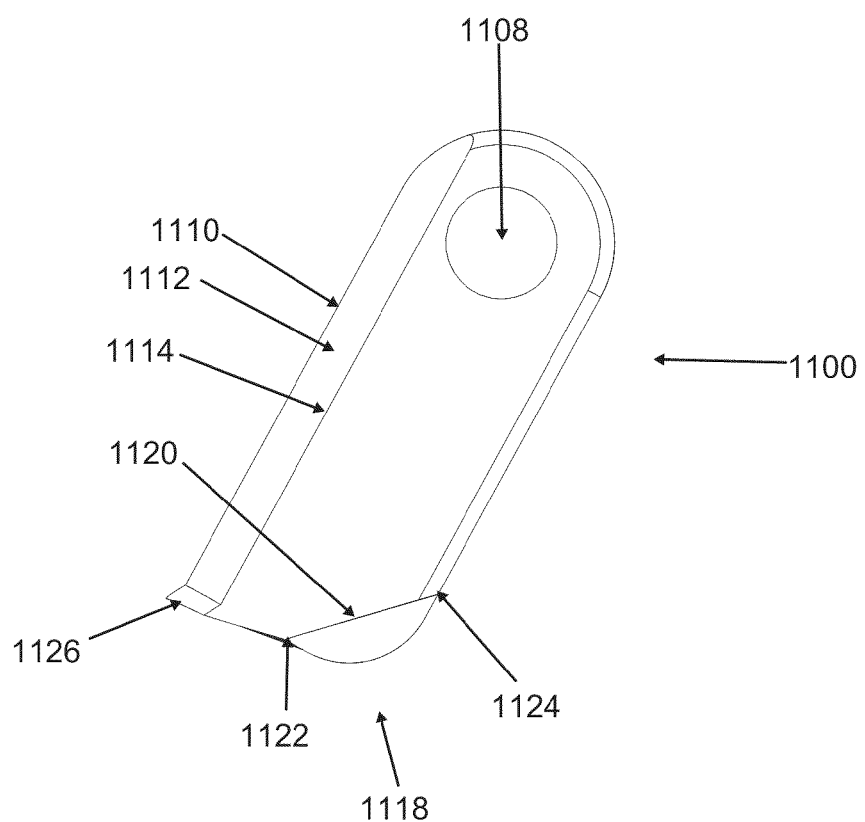
FIGS. 10B and 10C are posterior and side elevational views of the blade element of FIG. 10A.
Figure 10C:
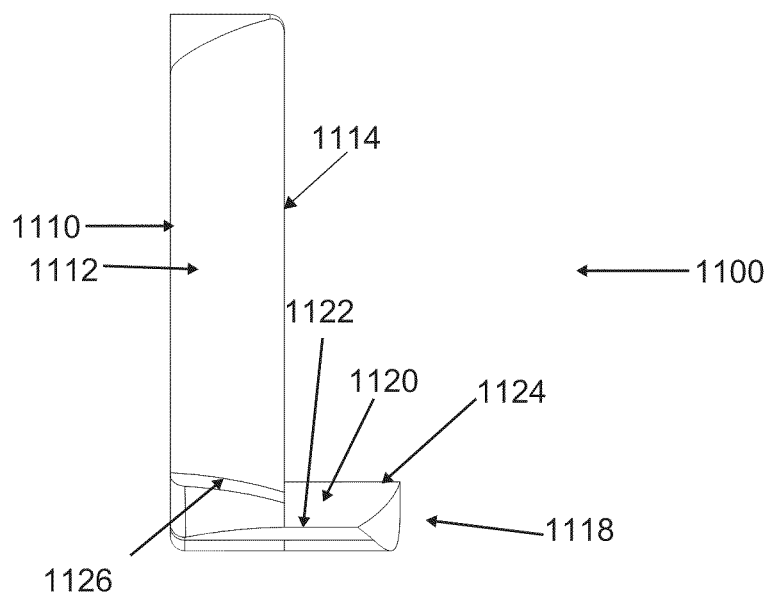

In some examples, the tissue removal mechanism located about the distal end of the tissue removal device may comprise a variable configuration, which may permit a reduced profile for device insertion and an expanded profile to increase tissue removal volume and/or speed. In other examples, the tissue removal mechanism may have a fixed configuration. FIG. 10A depicts one example of a tissue removal mechanism 1100 attached to an inner shaft 1102 of a tissue removal device 1104, comprising an elongate cutting block 1106 having a transverse orientation with respect to the inner shaft 1102. Referring to FIGS. 10A to 10C, the cutting block 1106 is coupled to the inner shaft 1102 at a central attachment site 1108. The cutting block 1106 comprises a leading cutting edge 1122, a trailing surface 1120 bordered by the leading cutting edge 1122 and a trailing edge 1124 located opposite the leading cutting edge 1122. In this example, the cutting edge 1122 has a generally parallel orientation with respect to the inner shaft 1102, and has a generally linear configuration and has a relative radially outer location relative to the inner shaft 1102. The trailing edge 1124 also has a generally linear configuration but a relative radially inward location with respect to the inner shaft 1102. In other examples, the cutting edge and/or the trailing edge may have a non-linear configuration and may be oriented at any of a variety of angles with respect to the inner shaft 1102. The trailing surface 1120 of the leading cutting edge 1122 has a generally planar configuration and forms a generally acute angle with respect to a radial line 1121 drawn from to the inner shaft 1102 to the leading cutting edge 1122. Thus, the trailing surface 1120 has a radially inward sloping orientation from the leading cutting edge 1122 to the trailing edge 1124. With some uses, the radially inward sloping orientation of the trailing surface 1120 may facilitate radially inward displacement of surrounding fluid or disrupted tissue, which in turn may direct these materials toward the auger mechanism 1116 of the device 1104 for removal out of the access site. In other examples, the trailing surface may have a non-planar configuration, or may be generally perpendicular or form an acute angle with the inner shaft. Additional cutting edge 1126 may also be provided elsewhere.

As shown in FIGS. 10A to 10C, in some examples, the cutting block 1106 may also comprise one or more additional flow control mechanisms. Here, the flow control mechanism comprises a flow control surface 1112 comprising a leading edge 1110 having a generally radial orientation and a relative distal location, a trailing edge 1114 having a generally radial orientation and a relative proximal location, such that the flow control surface 1112 has generally a distal to proximal sloping orientation with respect to the intended direction of rotation. In some examples, this may facilitate proximal displacement of material cut by the cutting edge 1110 and to flow toward the auger mechanism 1116. As shown, both the leading edge 1110 and the trailing edge 1114 of the flow control surface 1112 have linear configurations, with a planar flow control surface 1112, but in other examples, one or both edges may be non-linear or curved and the flow control surface may be non-planar, angled or twisted, for example. In some examples, the leading edge 1110 of the flow control surface 1112 may also be sharpened or otherwise configured to cut or grind tissue. Each edge of the cutting block associated with cutting and/or additional flow control may or may not lie in the same plane.

Although the cutting block 1100 in FIGS. 10A to 10C is configured to cut in a single direction, in other examples, the cutting block may be configured to cut when rotated in the opposite direction. The cutting block may be configured with similar or different cutting characteristics in the opposite direction, or may be configured with a different function altogether, e.g. facilitating distribution of fluids or materials into and/or out of the body site and/or the device itself.

Figure 11A:
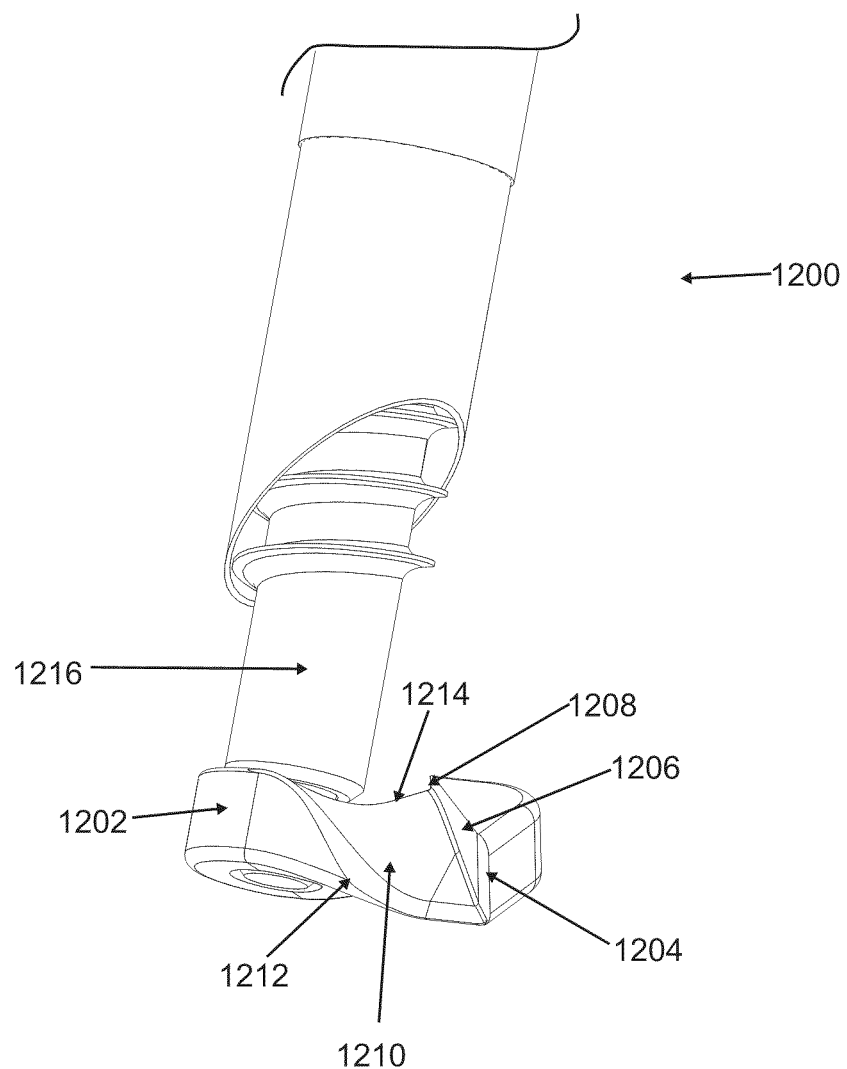
FIG. 11A is a perspective view of a distal end of another tissue removal device with a rotatable blade element.
Figure 11B:
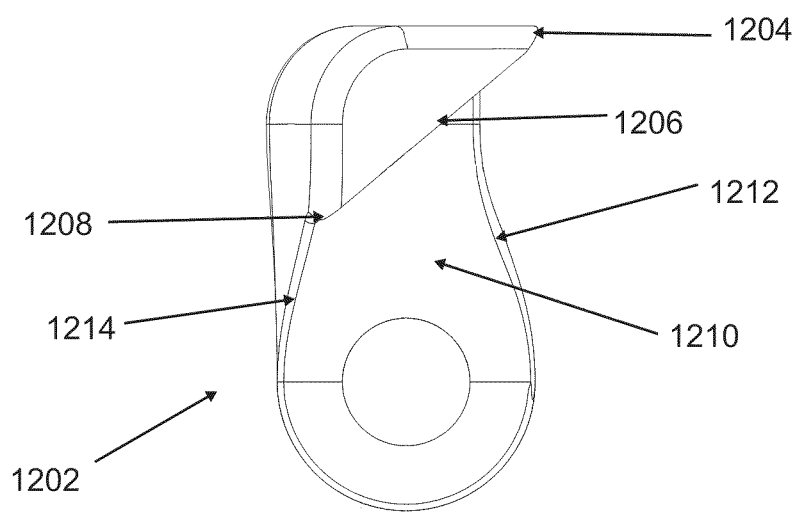
FIGS. 11B and 11C are posterior and side elevational views of the blade element of FIG. 11A.
Figure 11C:
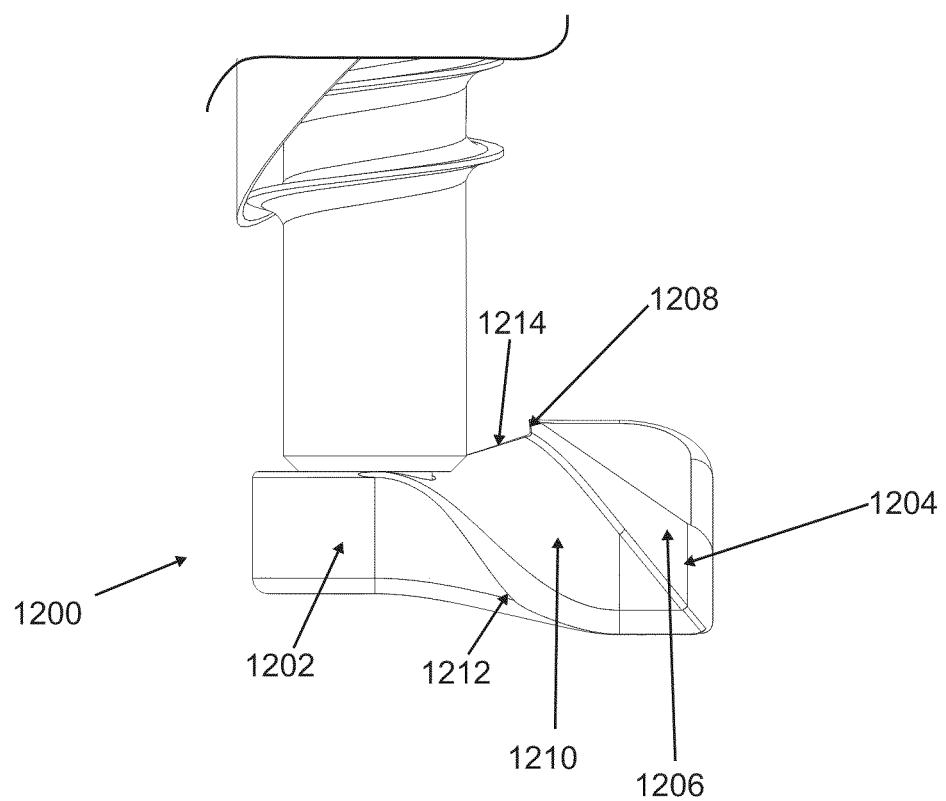

FIG. 11A depicts another example of a tissue removal mechanism 1200, comprising a cutting block 1202 with a leading cutting edge 1204. The leading cutting edge 1204 has a generally radially outward location with a planar radially inward trailing surface 1206, while the trailing edge 1208 of the trailing surface 1206 has a generally proximal and radially inward location. The orientation of both edges 1204 and 1208 are generally parallel to the rotation axis of the inner shaft 1216. The cutting block 1202 also comprises a distal-to-proximal sloping flow control surface 1210 where the leading edge 1212 with a non-linear, twisted configuration that goes from distal radially outward location to a proximal, radially inward location and does not lie within a single plane. The trailing edge 1214 comprises a curved configuration but has a radially outward section that curves proximally than its radially inward section. The distal-to-proximal sloping flow control surface 1210 has a non-planar, twisted configuration.

Figure 12:
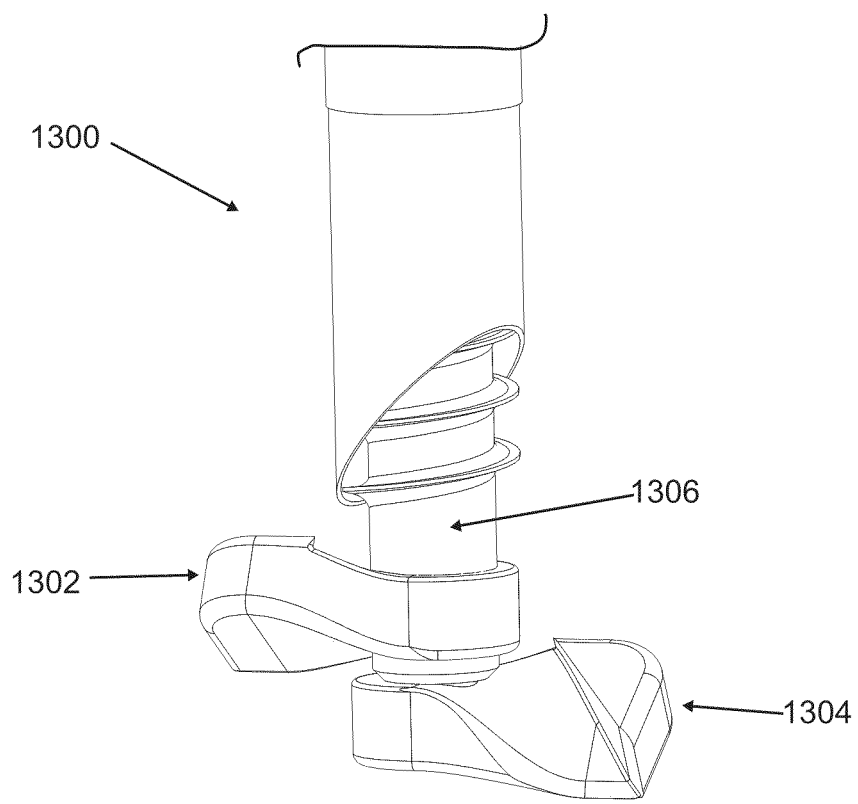
FIG. 12 is a perspective view of a distal end of another tissue removal device comprising dual rotatable blade elements.

Although the preceding examples of tissue removal devices in FIGS. 10A to 11C comprise a single cutting block, in other examples, multiple cutting blocks may be attached to the inner shaft of the device. In FIG. 12, for example, the tissue removal device 1300 comprises a proximal and distal cutting block 1302 and 1304 having a similar configuration as the cutting block in FIGS. 11A to 11C. The cutting blocks are located about 180 degrees apart with respect to the inner shaft 1306 of the device 1300, but in other examples may have any of a variety of angular positions from about 0 degrees to about 180 degrees apart. The angular position of the cutting blocks may be fixed or variable. Devices with variable position cutting blocks may provide a adjustment mechanism in the proximal housing to change the position of the cutting blocks as described elsewhere herein. In other examples, the variable position may self-change upon rotation of the cutting blocks. For example, one cutting block may have a fixed position while a second cutting block may be biased to an overlapping position with the first cutting block when stationary. Upon rotation of the cutting blocks, the resistance encountered by the second cutting block may overcome the bias force and cause pivoting until the second cutting block pivots against a limit structure (e.g. a blocking structure located which stops the second cutting block from further pivoting. In some examples, the bias force may be about zero, i.e. the second cutting block may freely swing. In other examples, three or more cutting blocks may be provided. Although having multiple cutting blocks may facilitate insertion of the device through smaller passageways by overlapping the location cutting blocks and separating them in use, in other examples, multiple cutting blocks may be integrally formed in a unibody or other fused structure.

The cutting blocks 1302 and 1304 are configured to rotate in the same direction, but in other examples may be configured to rotate in opposite directions. Also, in other examples, the cutting blocks may have a different configuration. In the depicted example, the cutting blocks are closely spaced along the longitudinal axis of the inner shaft 1306, but in other examples, two adjacent cutting blocks may be spaced apart a distance in the range of about 1 mm to about 10 mm or more, sometimes about 1 mm to about 5 mm, and other times about 2 mm to about 4 mm.

Figure 13:
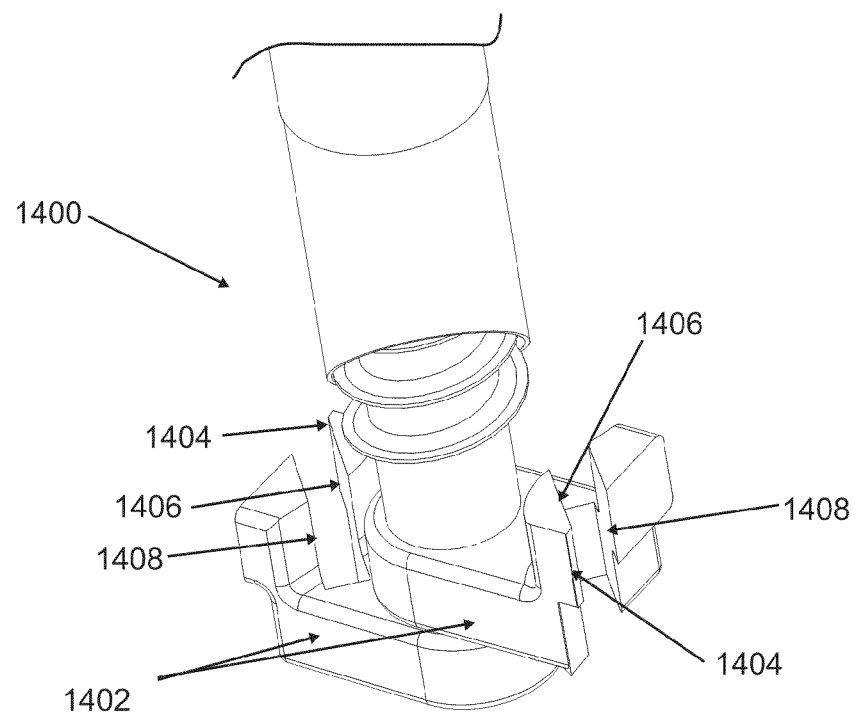
FIG. 13 is a perspective view of a distal end of another tissue removal device with dual rotatable blade elements.

FIG. 13 illustrates another example of a tissue removal device 1400 comprising multiple cutting blocks 1402. Here, the cutting blocks 1402 comprises a leading cutting edge 1404 with a trailing surface 1406 that slopes radially inward and forms a channel with a corresponding flow control surface 1408 that is also configured with a radially inward slope. In this particular example, no distal-to-proximal flow control surfaces are provided.

Figure 14:
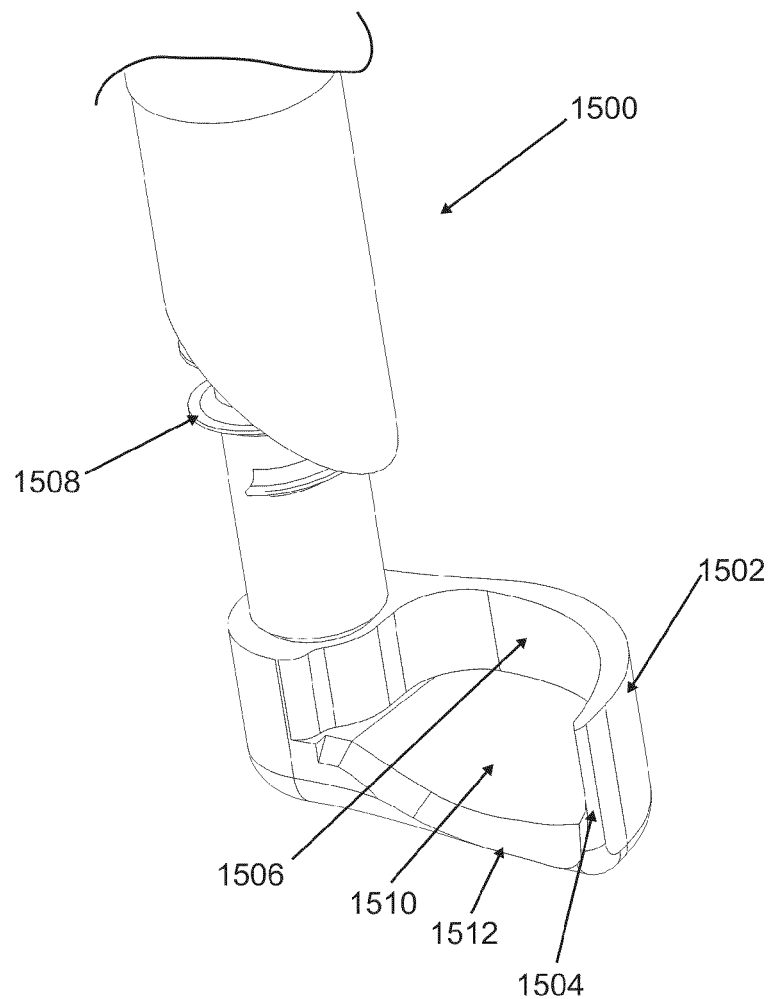
FIG. 14 is a perspective view of a distal end of another tissue removal device with a rotatable blade element.

FIG. 14 illustrates another example of a tissue removal device 1500 comprising a cutting block 1502 with an outer cutting edge 1504 with a concave trailing surface 1506. The device 1500 may further comprise a flow control surface 1510 comprising a concave leading edge 1512 with an orientation that is generally orthogonal to the concave trailing surface 1506 of the outer cutting edge 1504. In some instances, the either or both the concave trailing surface 1506 and the concave leading edge 1512 may entrap or otherwise maintain disrupted tissue closer to the auger mechanism 1508, which may facilitate its removal.

The cutting blocks may project from the rotational axis of the inner shaft any in the range of about 1 mm to about 8 mm, sometimes about 2 mm to about 6 mm, and other times about 4 mm. The axial thickness of the cutting blocks may be anywhere in the range of about 0.1 mm to about 10 mm or more, sometimes about 1 mm to about 3 mm, and other times about 0.5 mm to about 10 mm. In some examples, the cutting block may be integrally formed with the inner shaft, or attached to the shaft by welding, brazing, soldering, gluing or overmolding. The cutting blocks may be made of hardened stainless steels such as 17-4 PH, or 400 series, or tungsten alloy, titanium alloy, cobalt chromium, silicone carbide, glass, ceramics, or combinations thereof.

Figure 15A:
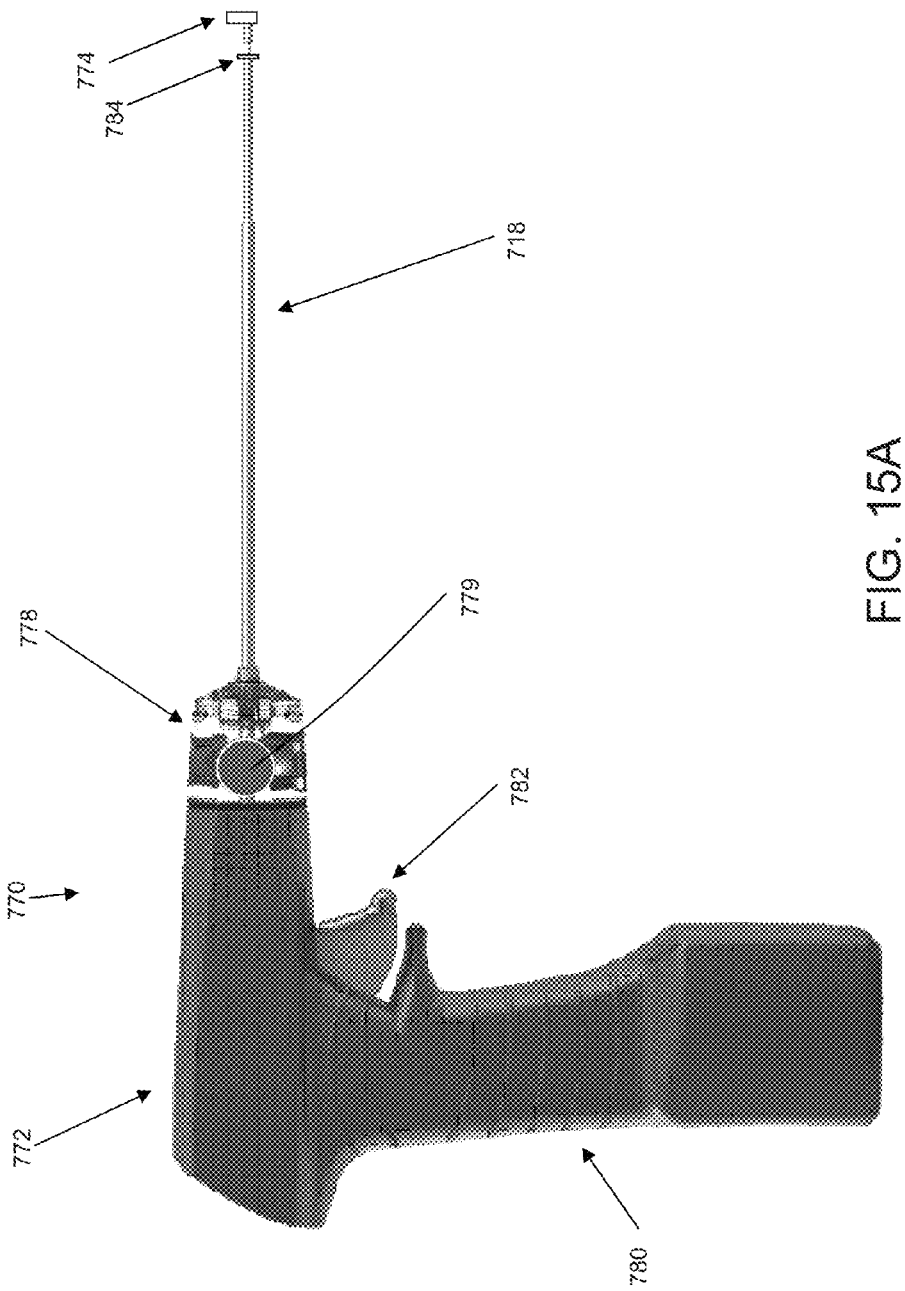
FIG. 15A illustrates one variation of a tissue-removal device comprising a handle portion, a shaft, and a tissue-removal assembly.
Figure 15B:
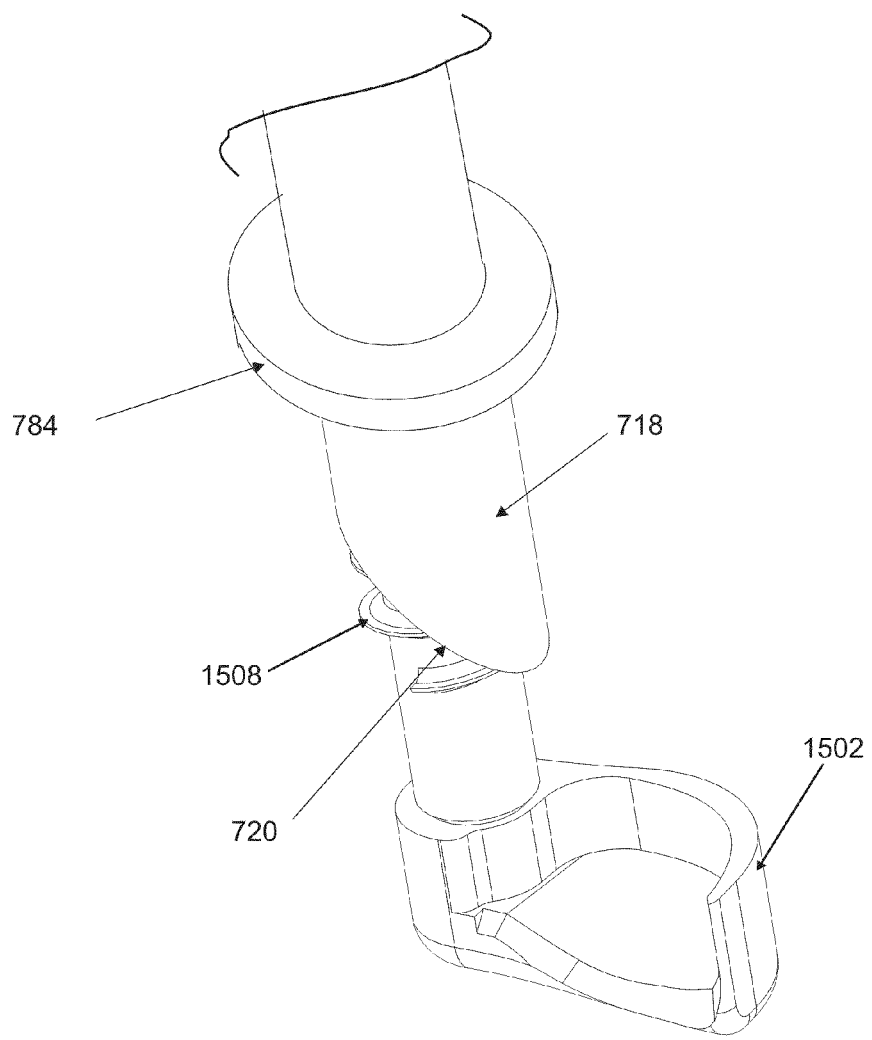
FIG. 15B depicts the tissue-removal device of FIG. 15B with the cutting block in FIG. 14 and a travel limiter.

Another variation of a device that may be used for surgical spinal procedures, e.g., interbody fusion procedures, is depicted in FIG. 15. The tissue-removal device 770 may comprise a proximal handle portion 772 and a distal tissue-removal assembly 774 connected to the handle portion 772 by a shaft 718 with a longitudinal lumen therethrough. Optionally, the shaft 718 may have an port or lumen for irrigation or infusion of liquid (e.g. saline) or therapeutic agents during the procedure. In some variations, the shaft 708 may be straight, or may have one or more pre-shaped curves or angles. The handle portion 772 may comprise a gripping portion 780 that has an ergonomic shape that is suitable for a one-handed grip. The handle portion 772 may also comprise one or more control features, such as rocker-type switches, knobs, dials, levers, sliders, etc. that actuate, navigate, or otherwise regulate the use of the tissue-removal device. For example, the handle portion 772 comprises a lever 782 that may be used to actuate the components of the tissue-removal assembly 774, and may additionally comprise a power switch, as well as a mechanism for navigating the tissue-removal assembly 774. In some variations, the navigation and movement of the tissue-removal device 770 may be constrained or restricted by a travel limiter. FIG. 15B depicts the tissue-removal device 770 of FIG. 15A configured with the cutting block 1502 of FIG. 14 and a travel limiter 784, which is described in greater detail below. Referring back to FIG. 51A, the travel limiter 784 may be located, for example, along the length of shaft 718 distal to the collection chamber 778. In certain variations, a travel limiter may be a separate device that is used in concert with the tissue-removal device 770.

Figure 16A:
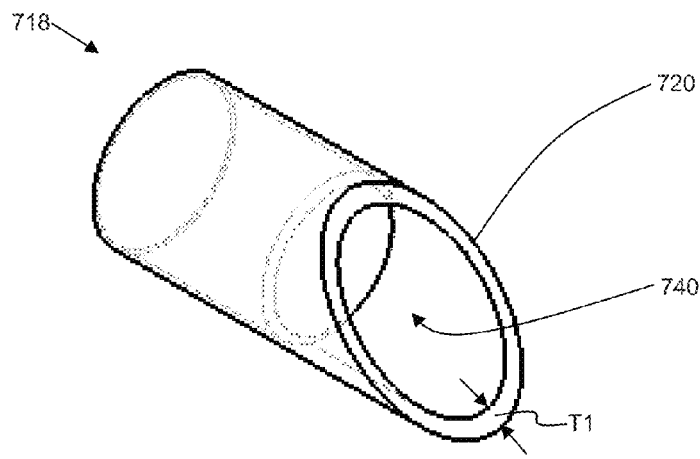
FIGS. 16A to 16B depict one variation of an outer tubular shaft with a beveled cutting edge.
Figure 16B:
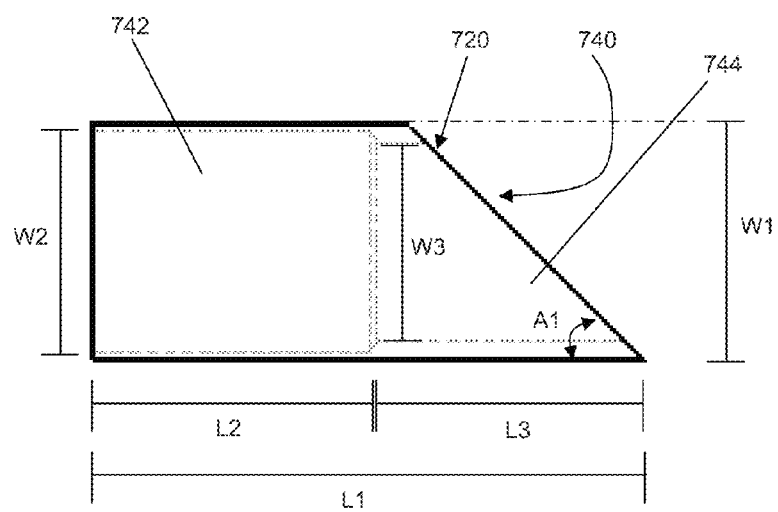

A perspective and side view of the outer tubular shaft 718 is depicted in FIGS. 16A and 16B. The cutting edge 720 may be beveled to have an angle A1 and a thickness T1. The angle A1 may be in a range from about 30° to about 90°, for example, about 35° or 50°. The thickness T1 may be in a range from about 0.002 inch to about 0.025 inch; for example, about 0.017 inch. The diameter or widest portion of the outer tubular shaft 718 may have a width W1, where W1 may be from about 0.085 inch to about 0.15 inch, for example, 0.102 inch, and the longest portion of the outer shaft may have a length L1, where L1 may be from about 0.2 inch to about 0.3 inch, for example, 0.236 inch. The outer tubular shaft 718 may have a lumen 740 therethrough, where the size and shape of the lumen cross-section may vary along the length of the outer tubular shaft. For example, as illustrated in FIG. 16B, a proximal portion 742 of the outer tubular shaft may have a rectangular cross-section, while a distal portion 744 may have a trapezoidal cross-section. The proximal portion 742 may have a width W2 and a length L2. The width W2 may less than W1, and may be from about 0.084 inch to about 0.14 inch, for example, 0.096 inch, and the length L2 may be from about 0.09 inch to about 0.12 inch, for example, 0.118 inch. The distal portion 744 may have a width W3 and a length L3. The width W3 may be less than W1, and in the example depicted in FIG. 16B, the width W3 may be less than W2. For example, the width W3 may be from about 0.083 inch to about 0.139 inch, e.g., 0.085 inch. The length L3 may be from about 0.08 inch to about 0.21 inch, for example, 0.118 inch. The outer tubular shaft may be made of stainless steel (e.g., 440F SE stainless steel, 17-4), and may be heat treated to RC 33-60, with a bright finish that may be passivated per ASTM-A967 standards. The outer tubular shaft may also be made of a variety of materials, such as other metallic materials (e.g., nickel titanium alloys, cobalt chromium, tungsten, etc.) and/or polymeric materials (e.g., PEEK, polyaramides, polyethylene, etc.), as appropriate.

Figure 17A:
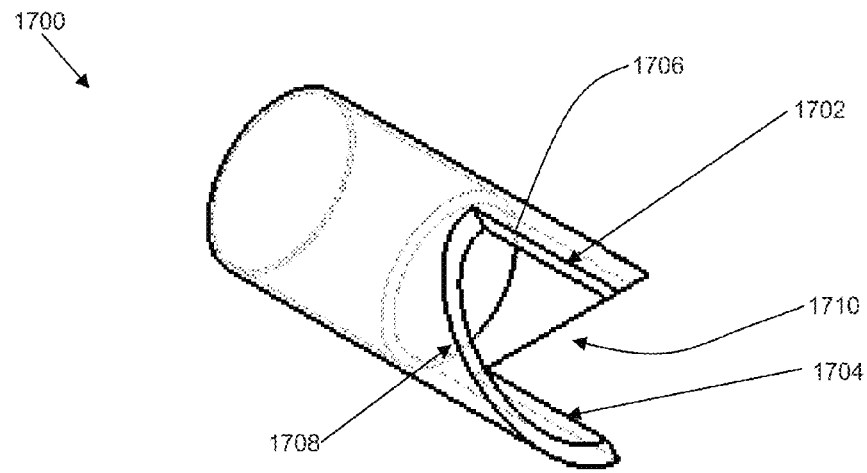
FIGS. 17A to 17B depict another variation of an outer tubular shaft with multiple cutting edges, comprising straight and curved edges.
Figure 17B:
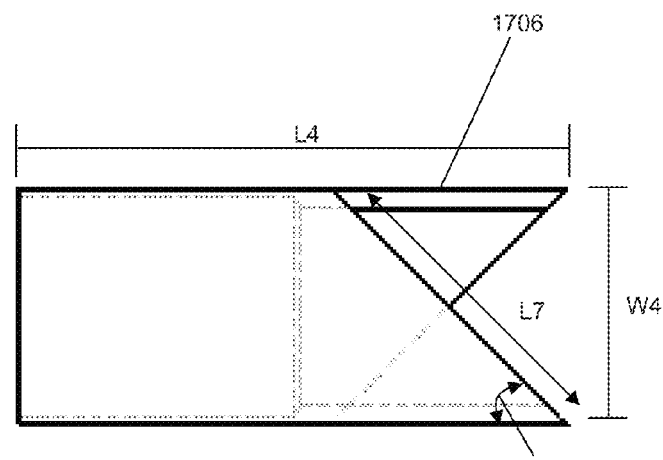

Some variations of an outer tubular shaft may have one or more sharpened edges that may be used with a tissue removal system. The additional sharpened edges may help to further scrape or break up tissue. One example of an outer tubular shaft 1700 with additional sharpened edges is depicted in FIGS. 17A and 17B. The outer tubular shaft 1700 may comprise a first cutting edge 1702 along the surface of the shaft 1700, and a second cutting edge 1704 that is opposite to the first cutting edge. The first cutting edge 1702 may comprise a straight edge 1706 that may be parallel to the longitudinal axis of the outer tubular shaft, and a curved edge 1708 that may be at least partially transverse to the longitudinal axis of the outer tubular shaft. The second cutting edge 1704 may have the same arrangement of edges, or may have different arrangements of edges. The contour of the curved edge may partially circumscribe the curved surface of the outer tubular shaft, and may also extend along the longitudinal axis of the shaft. FIG. 17B depicts a side view of the outer tubular shaft 1700. The angle A2 between the curved edge 1708 and the surface of the outer tubular shaft 1700 may be about 30° to about 90°, e.g., about 45°. The length L7 of the projection of the curved edge 1708 in the side view of FIG. 17B may be from about 0.1 inch to about 0.2 inch, e.g., 0.144 inch. The length L4 of the outer tubular shaft 1700 may be from about 0.2 inch to about 0.3 inch, e.g., 0.236 inch. The width W4 of the outer tubular shaft may be from about 0.085 inch to about 0.15 inch, for example, 0.102 inch. The size and shape of a lumen 1710 may vary, as described above.

Figure 19:
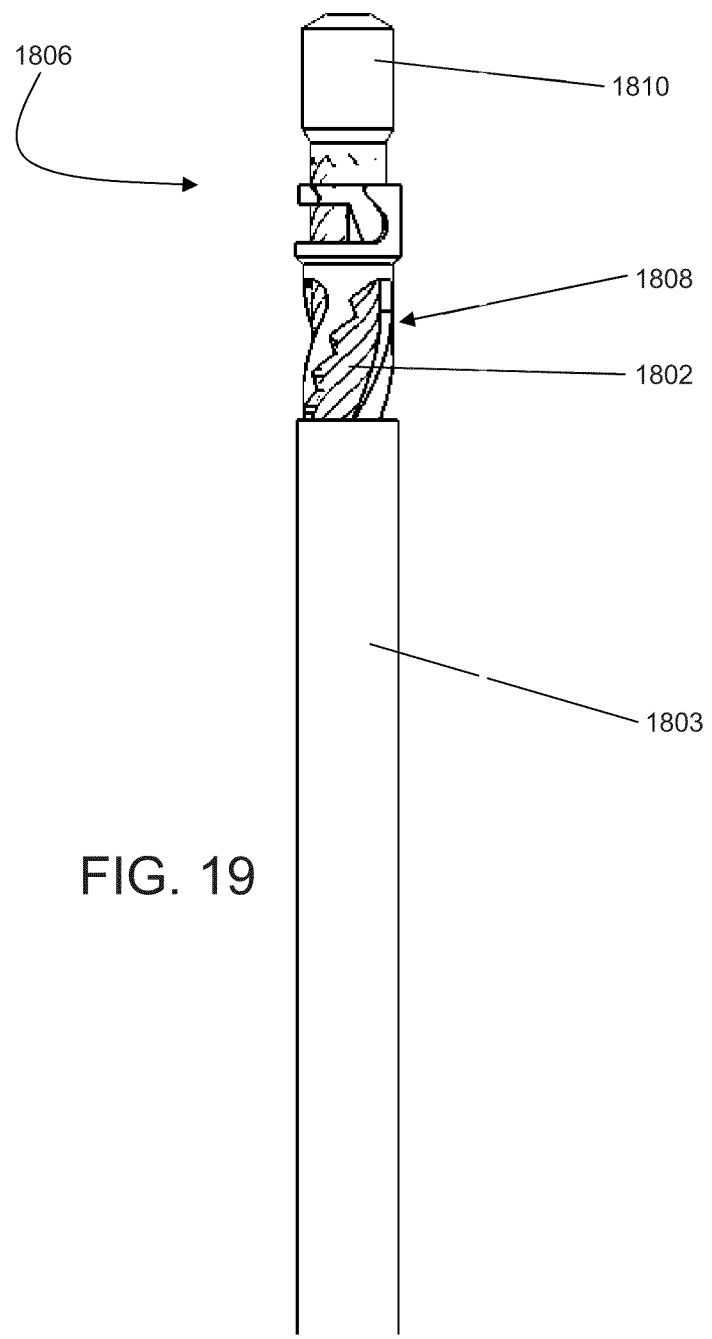
FIG. 19 depicts an example of a tissue transport assembly from FIG. 18A with a sheath.

As indicated previously, a tissue-removal assembly may be provided with a tissue transport assembly, which may help draw the removed tissue away from the tissue site and into a collector. One example of a tissue transport assembly 1800 that may be used with the tissue-removal assembly 5200 is shown in FIG. 18A. As seen there, the tissue transport assembly 1800 comprises a drive member 1802 that is attached at its distal end to an impeller 1806, and a helical member 1804 mounted on at a least a portion of the drive member 1806. One variation of a tissue transport assembly that may be used with a tissue removal assembly is shown in FIG. 18A. The tissue transport assembly 1800 may comprise a rotatable drive member 1802, a helical member 1804 mounted on at least a portion of the rotatable drive member 1802, and an impeller 1806 attached at a distal portion of the drive member 1802. The rotatable drive member 1802 may be made of one or more polymeric and/or metallic materials that are suitable for drawing tissue up proximally from the tissue removal assembly to the collector. For example, the rotatable drive member 1802 may be made of stainless steel, nickel titanium alloy, carbon fiber, high density molecular weight polyethylene, and the like. The inner diameter of the rotatable drive member 1802 may be from about 0.010 inch to about 0.020 inch, e.g., 0.015 inch. The outer diameter of the rotatable drive member 1802 may be from about 0.0350 inch to about 0.0450 inch, e.g., 0.0407 inch. The helical member 1804 may be integrally formed with the rotatable drive member 1802, or may be separately formed and attached to the drive member. The pitch P1 of the helical member 1804 may be from about 0.010 inch to about 0.100 inch, e.g., 0.030 inch to about 0.25 inch, or about 0.060 inch to about 0.100 inch, or 0.030 inch, or 0.080 inch. The pitch P1 of the helical member may be adjusted according to the rotational speed driven by the motor, or according to the desired rate of tissue transport from the tissue removal assembly to the collector. The helical member 1804 may be made of materials similar to the rotatable drive member 1802, and may optionally include surface modifications such as friction-reducing coatings, fluid dynamic channels, etc., which may help to transport the removed tissue to the collector. The helical member 1804 may be right hand wound, or left hand wound, as appropriate for tissue transport. In some examples, the helical member 1804 may be wound in the same sense as the rotation of the drive member. In certain variations, a rotatable drive shaft may be an integrally formed tube, e.g., a tube formed from a solid sheet of material that is not woven or braided, with the helical member coiled along the outer surface of the tube. In other variations, the rotatable drive shaft may be made of multiple layers of tightly wound coiled members, where the inner layers of the coiled members may have a first pitch, the outer layers of the coiled members may have a second pitch. For example, the pitch of the coiled members may vary from the innermost layer to the outermost layer, e.g., the innermost coil layer may have the tightest pitch, and the outermost layer may have the highest pitch. In this variation, polymers or other adhesives, such as epoxy, parylene, polyurethane, and the like, may be applied in between coiled layers or as an outer coat, to secure the threads of the outermost coiled member to the next inner coiled layer. These adhesives coatings and layers may help prevent the coiled layers from separating and lifting off each other. In general, the tissue transport assembly 1800 may comprise one or more recesses, grooves, channels, protrusions, and the like which may expedite tissue transport as desired. Other characteristics of drive members and helical members have been described previously, and may also be used with the tissue transport assembly 1800. FIG. 19 depicts the tissue transport assembly 1800 of FIG. 18A residing in an overtube 1803 of a tissue removal device.

The distal portion of the drive member 1802 may be coupled to the impeller 1806, which may have one or more recesses, grooves, channel, etc. which may help expedite tissue transport. An enlarged depiction of the impeller 1806 is shown in FIG. 18B. The proximal portion of the impeller 1806 may comprise a helical cage 1808, and the distal portion may comprise an impeller cap 1810. The impeller 1806 may also comprise one or more grooves and/or cutout regions, for example, slanted groove 1812 and cutout region 1814 on the impeller cap 1810. The slanted groove 1812 and/or the cutout region 1814 may be sized and shaped for passing a cable (e.g., support or extendable element) over the surface of the impeller 1806, similar to the grooves and recesses that may be used with a rotatable shaft as previously described. The drive member 1802 may be inserted into the helical cage 1808, and/or may be attached by welding, gluing, soldering, and the like. The impeller cap 1810 may be made of a polymeric material such as PEEK, Pebax, nylon, polyethylene, polyimide, and the like, and may have a length L13 of about 0.150 inch to about 0.300 inch, e.g., 0.235 inch. In some variations, an insulating coating may be provided on a portion of the impeller to help reduce the risk of thermal nerve injury during the procedure.

Figure 18D:
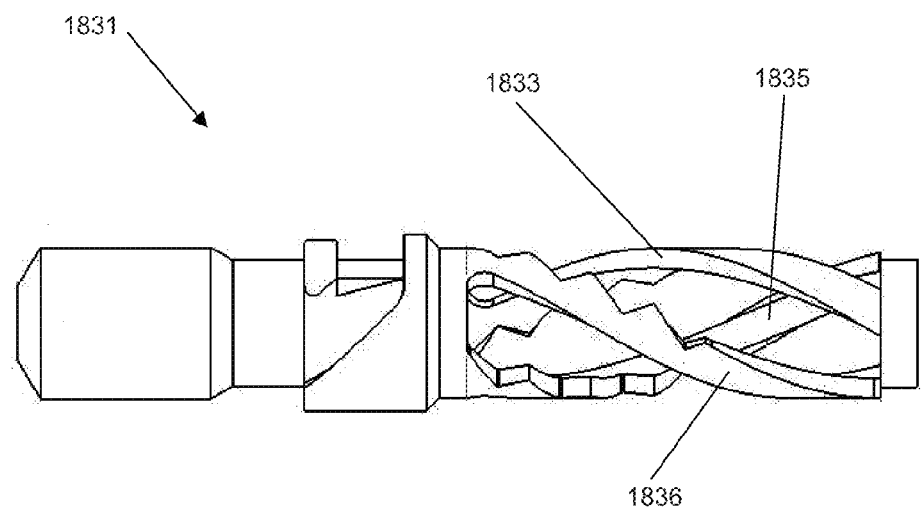
Figure 18E:
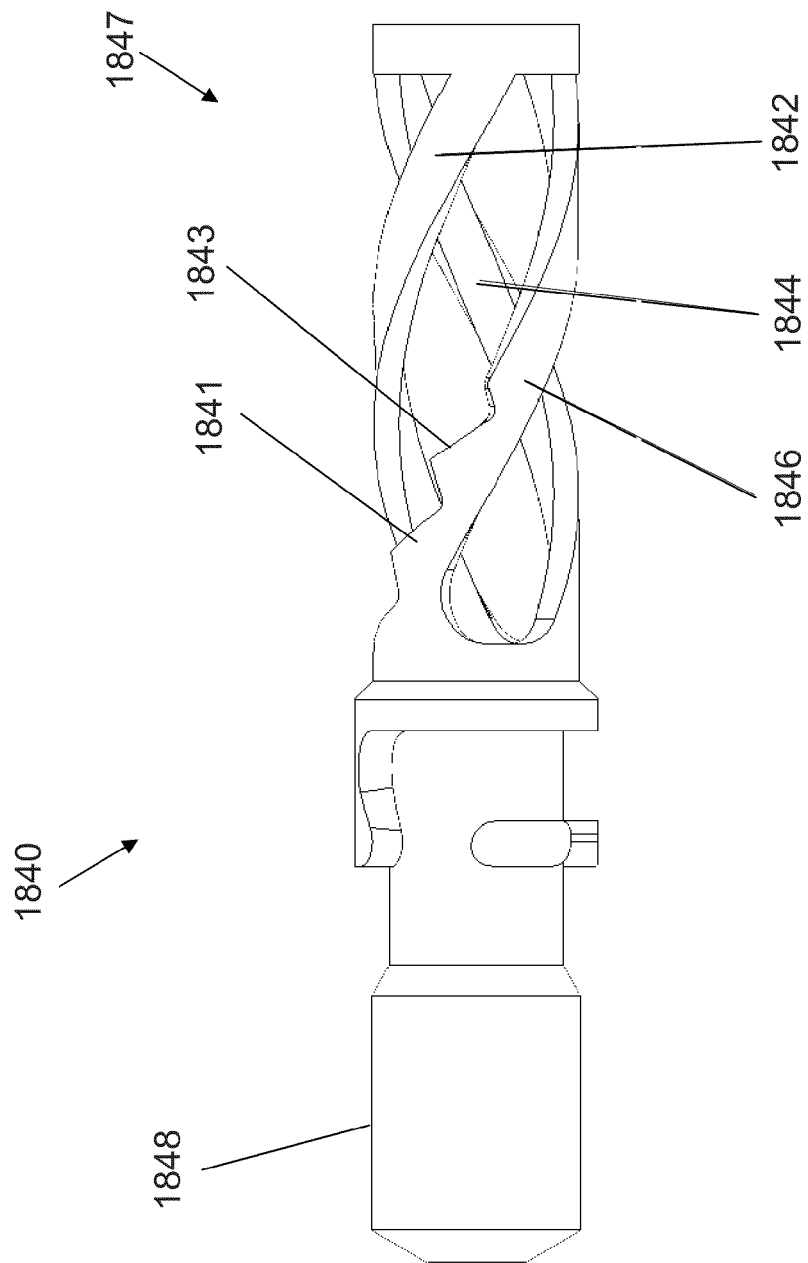
Figure 18F:
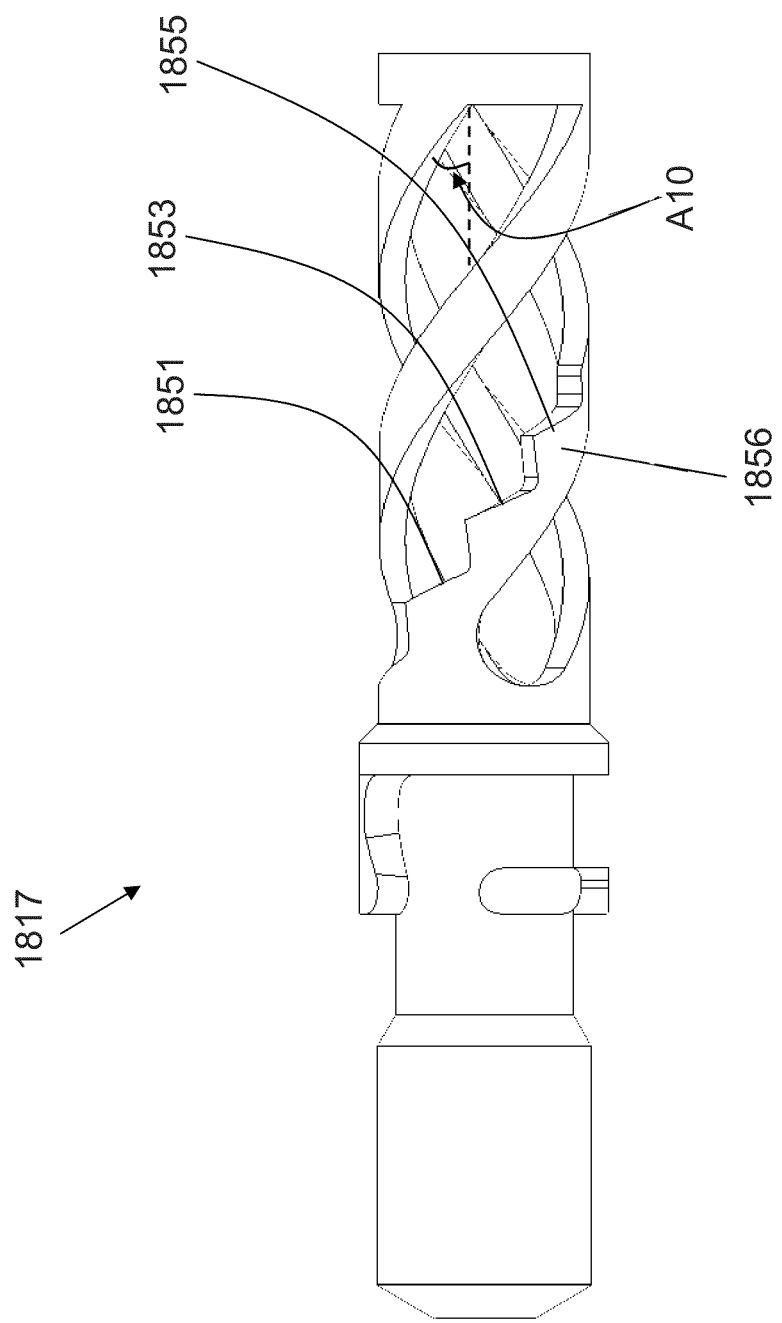

The helical cage 1808 may be made of a metallic material such as stainless steel or polymeric material such as PEEK. Certain variations of an impeller may comprise two more braids similar to braid 1807. As seen in FIG. 18B, the impeller 1806 may comprise three braids that have a clockwise pitch angle of about 30° to about 60°, e.g., 35°. The braids 1807 may have a rate of turning along the length L14 of the helical cage 4108 of about 3 turns/inch to about 5 turns/inch, e.g., 4.5 turns/inch. The length L14 of the helical cage 1808 may be from about 0.150 inch to about 0.300 inch, e.g., 0.230 inch. The braid 1807 may have a width from about 0.015 inch to about 0.030 inch, e.g., 0.028 inch. The helical cage 1808 may have any number of braids or surface structures such as serrations, ridges, etc., that may be useful for drawing tissue from the tissue removal assembly to the collector. For example, one braid 1809 may be serrated with one or more teeth 1805, while other braids 1807 and 1808 may not have any teeth. The cage teeth 1805 may be located on a leading edge of each braid as determined by the braid angle and direction of rotation. The sharpened edge of the cage teeth 1805 may be on the leading edge. The cage teeth 1805 may help to further break up the tissue as it is drawn proximally away from the target tissue site. The teeth 1805 may be slanted at an angle, for example, the slant angle may be between about 20° to about 40°, and/or about 60° to about 80°. The edges of teeth 1805 may be any length appropriate for cutting or pulverizing tissue, e.g., from about 0.001 inch to about 0.004 inch, e.g., 0.002 inch. Other variations of teeth may be larger, with edge lengths of about 0.01 inch to about 0.02 inch. The two edges of the cage teeth 1805 may have a first short edge, and a second long edge, while in other variations, the edges may be the same length. Some variations of cage teeth may be C-shaped, and/or may have other angular geometries with sharp turning edges. Other cutting features or edges may be provided along the impeller and/or drive shaft, such as sharpened helical members, enzymatic coatings, etc. that may break up tissue and expedite its transport to a collector. The serrations may help to further break up the tissue as it is drawn proximally away from the target tissue site. Alternatively, as depicted in FIG. 18C, the impeller 1830 may have braids 1837, 1838, and 1839 without any serrations. In another variation of an impeller 1831 shown in FIG. 18D, all of the braids 1833, 1835, and 1836 may be serrated or have one or more teeth.

Figure 18G:
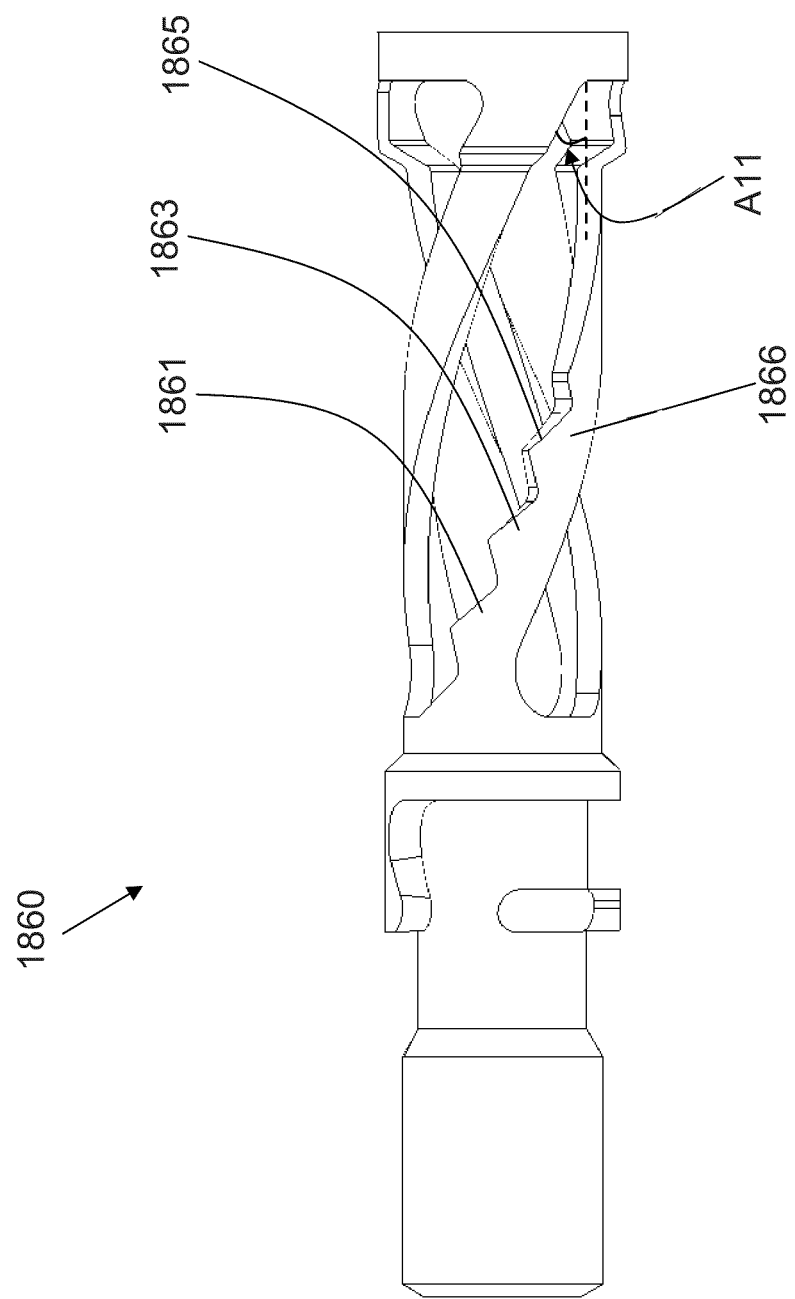
Figure 18H:
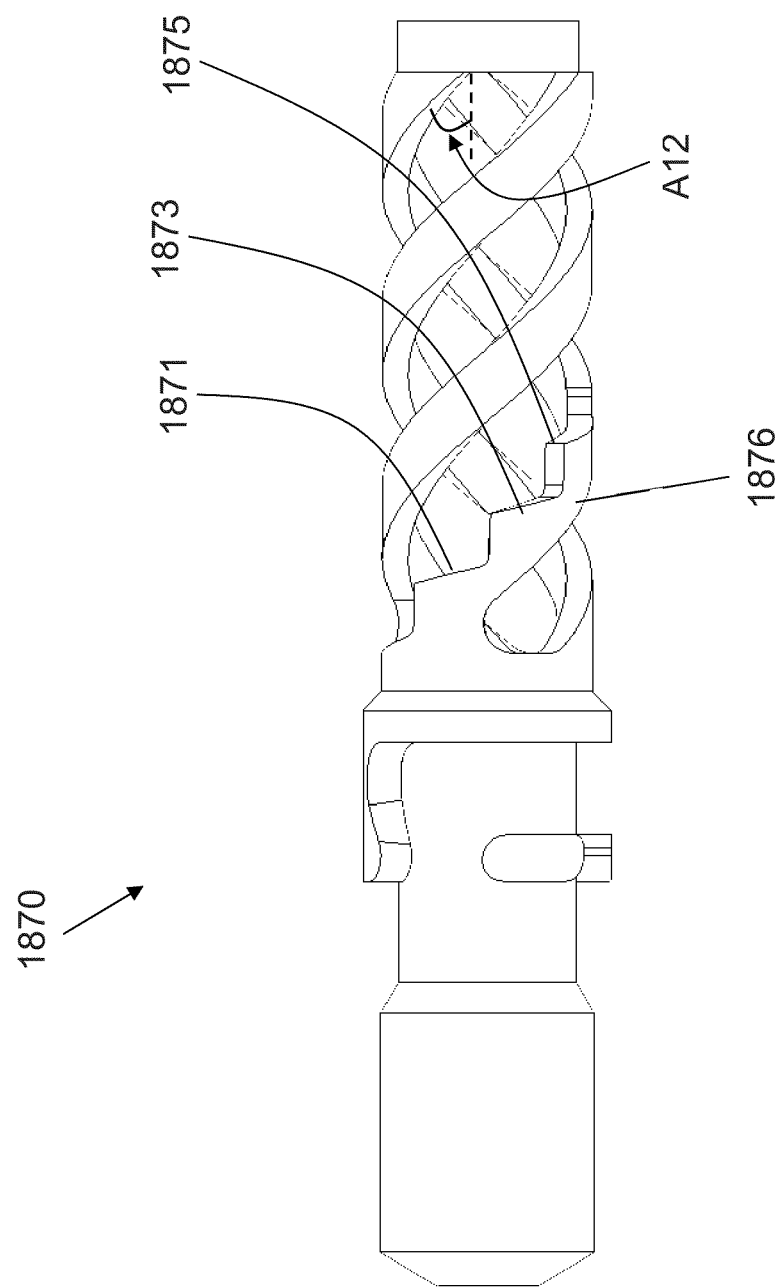
Figure 18I:
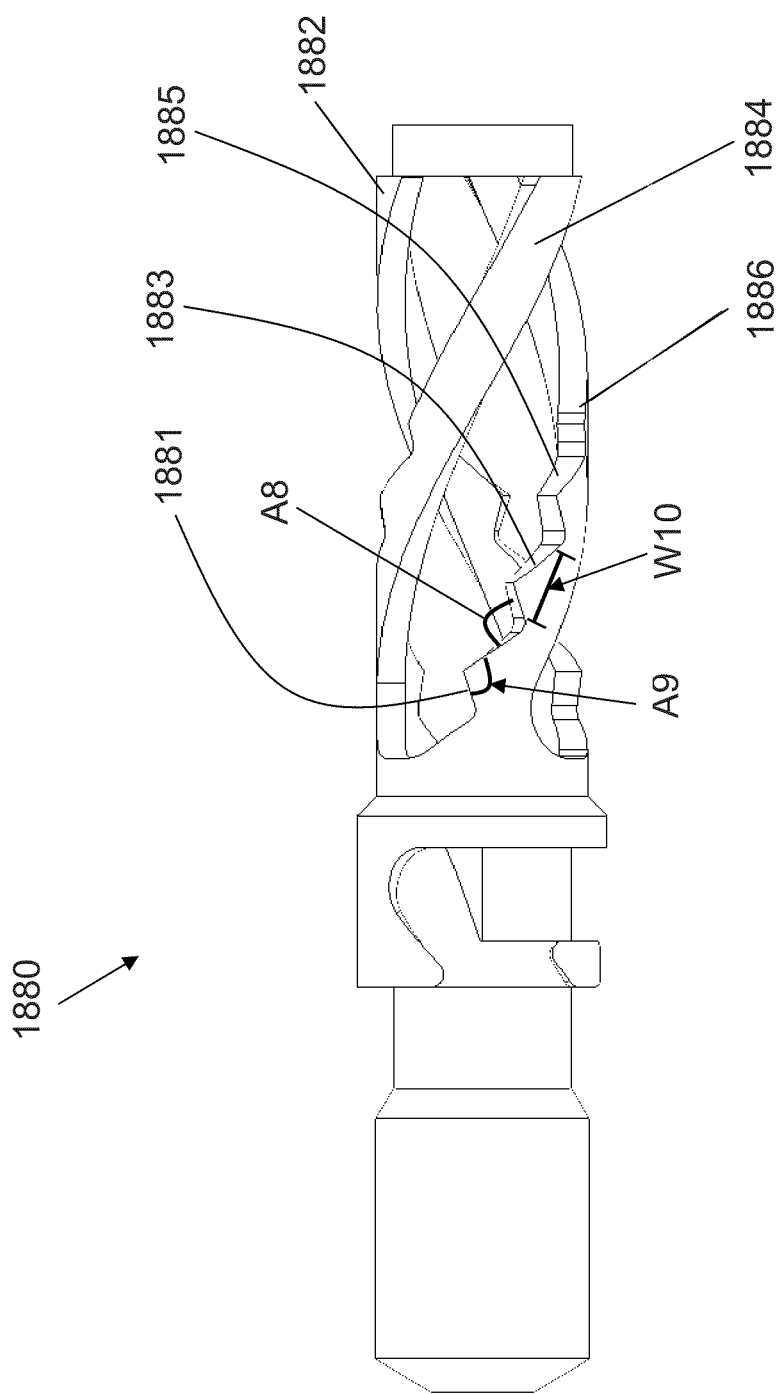

Additional variations of impellers are illustrated in FIGS. 18E to 18I. For example, the variation of an impeller 1840 shown in FIG. 18E may comprise an impeller cap 1848 with an angled distal tip and helical cage 1847. The helical cage 1847 may have a first braid 1842, a second braid 1844, and a third braid 1846. One or more of the braids may have serrations, and there may be any number of serrations on a single braid. For example, the third braid 1846 may have two serrations 1841, 1843. In another variation of an impeller 1850 depicted in FIG. 18F, a braid 1856 may have three serrations 1851, 1853, and 1855. The braids of the impeller 1850 may have a braid twist angle A10 of about 40°. FIG. 18G depicts an impeller 1860 with three braids that have a twist angle A11 of about 30°. The braid 1866 may have three serrations 1861, 1863, and 1865. FIG. 18H depicts an impeller 1870 with three braids that have a twist angle A12 of about 50°. The braid 1876 may have three serrations 1871, 1873, and 1875. In other variations, such as impeller 1880 depicted in FIG. 18I, all the braids 1882, 1884, 1886 have one or more serrations on a leading edge of each braid, for example, three serrations 1881, 1883, 1885. Serrations may have a positive rake (e.g., from about 30° to 40°) or negative rake and/or may be slanted at an angle, as previously described. The angle A8 between the serrations 1881, 1883, 1885 may be from about 80° to 150°, e.g., 105°, or 104.6°. The sharpened or pointed portion of a serration may have an angle A9, where A9 may be from about 45° to 120°. The edges of the serrations 1881, 1883, 1885 may be from about 0.001 inch to about 0.004 inch, e.g., 0.002 inch. Other variations of serrations may be larger, with edge lengths of about 0.01 inch to about 0.02 inch. Serrations may have a width W10 that may be from about 0.01 inch to about 0.2 inch, e.g., 0.04 inch.

Figure 20:
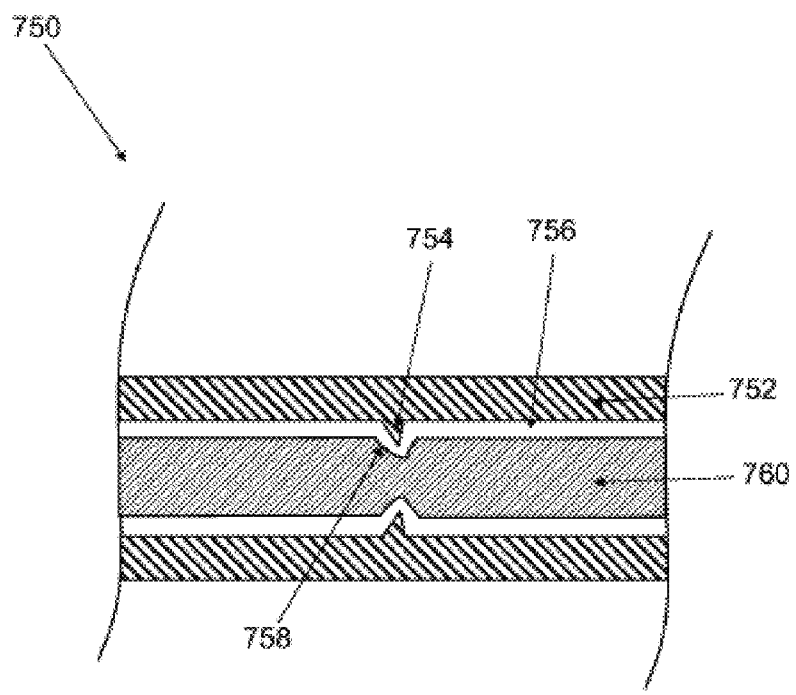
FIG. 20 is a schematic longitudinal cross-sectional view of another tissue removal device with an internal cutting mechanism.

FIG. 20 schematically depicts another example of a cutting mechanism where instead of a cutting edge 720 located at the distal opening of the outer tubular shaft 718 as depicted in FIG. 15B, the tissue removal system may comprise an internal cutting or grinding mechanism 750. This mechanism comprises an outer tubular shaft 752 with an inner cutting or grinding structure 754 that protrudes into the inner lumen 756 of the outer tubular shaft 752 and cooperates with a circumferential groove or recess 758 on the inner tubular shaft 760 to morcellize, cut or otherwise breakdown any larger tissue fragments that may enter the outer tubular shaft 752. The inner cutting structure 754 may have any of a variety of configurations, including different rake angles and/or surface configurations. The configuration of the recess 758 on the inner tubular shaft 760 may vary in width and cross-sectional shape. Although only a single internal mechanism 750 is depicted, in other examples, multiple mechanisms may be provided along the shafts 752 and 760. In some further examples, an internal mechanism 750 may be used with the tip-based mechanism illustrated in FIGS. 10A to 14.

The movement, orientation, and stability of a tissue-removal device may be regulated by a travel limiter, which may help to prevent inadvertent movement and/or shifting that may result in tissue injury. A travel limiter may be used to constrain and/or define the range of axial, rotational, and/or transverse movement of a tissue removal device after it has been inserted into a patient. For example, a travel limiter may be configured to regulate and/or restrict the position and orientation of a distal tissue-removal assembly. Travel limiters may have a number of configurations that allow varying degrees of motion to the tissue removal device. Some variations of a travel limiter may be permanently coupled to an access cannula, while other travel limiters may be temporarily coupled to a shaft of a tissue-removal device during use. One variation of a travel limiter 2100 that may be temporarily coupled with the tissue-removal devices described above is depicted in FIGS. 21A and 21B. The travel limiter 2100 may comprise a guide opening 2104 located at the distal end of an elongate body 2106, where the guide opening 2104 may be configured receive a tissue-removal device therethrough. The guide opening may be sized and shaped to restrict the movement of a tissue-removal device along the plane of the guide opening 2104. The guide opening 2104 may have one or more curves, bends, and/or angles that may help to constrain the displacement of a tissue-removal device within the bounds of the guide opening.

Figure 21A:
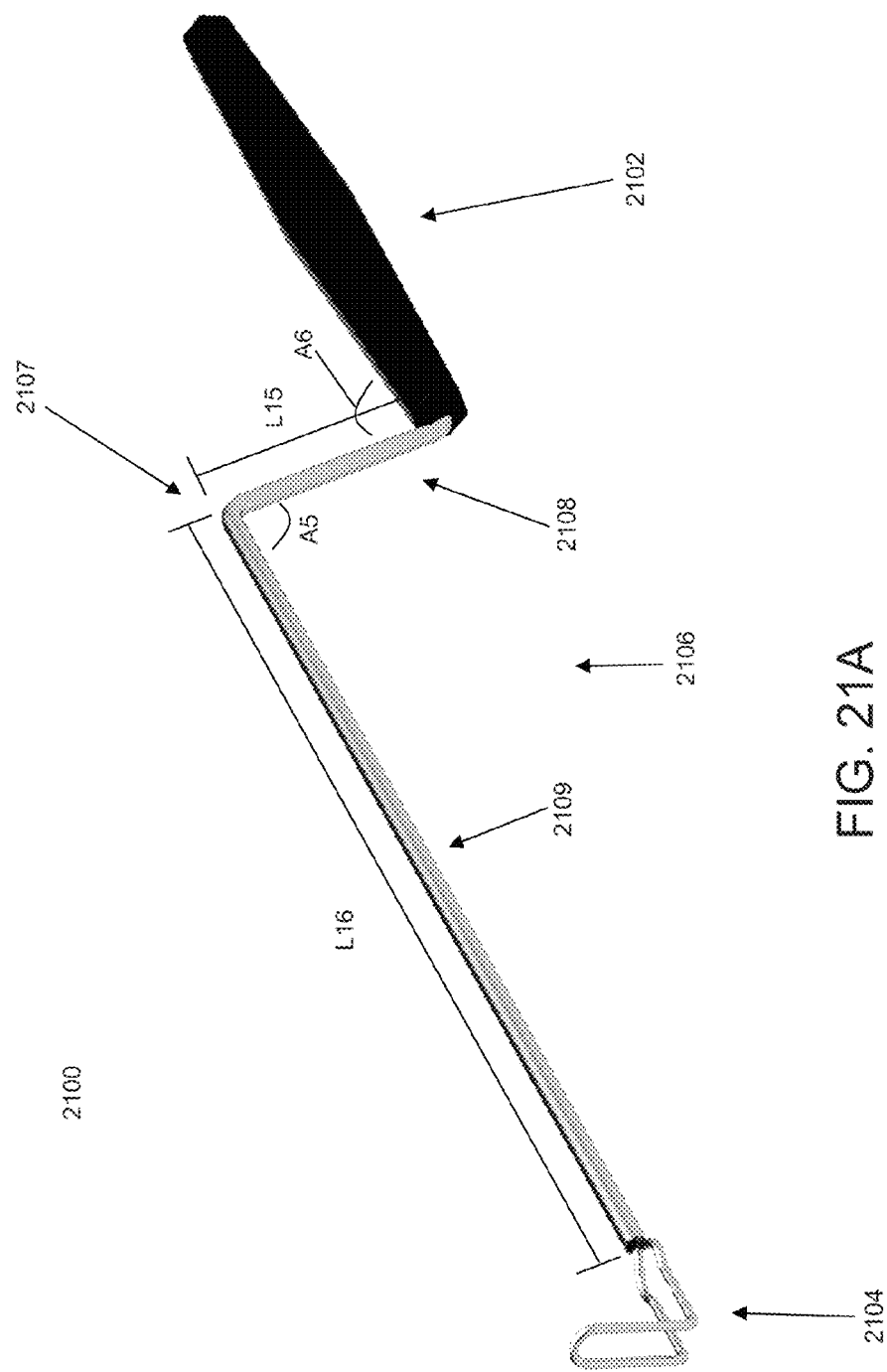
FIGS. 21A to 21F depict one variation of a travel limiter that may be used with a tissue-removal device.
Figure 21B:
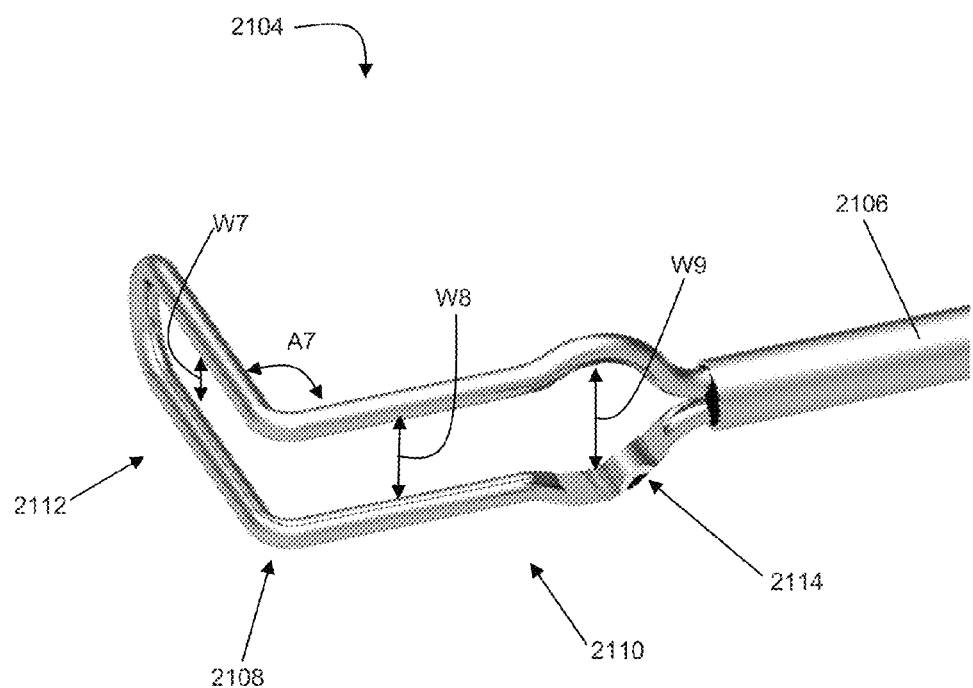

As depicted in FIG. 21B, the guide opening 2104 may comprise a loop of a metallic or polymeric material, where a first portion of the loop may be on a first plane, and the second portion of the loop may be on a second plane, where the first and second portions of the loop are separated by a bend 2108. In some variations, the first or second portion of the guide opening defined by the bend may be used to stabilize the travel limiter and/or the tissue-removal device against a tissue structure. Alternatively or additionally, the first and second portions of the guide opening defined by the bend may constrain the movement of a tissue-removal device in the guide opening along the first and second planes. For example, a tissue-removal device inserted through the first portion of the guide opening may be constrained to move along the first plane, within the boundaries of the first portion. The tissue-removal device may be translated across the bend to the second portion of the guide opening, where it may be constrained to move along the second plane, within the boundaries of the second portion. In some variations, the first and second portions may be co-planar, while in other variations, the first and second portions may be in unique planes. For example, the guide opening 2104 may have a first portion 2110 in a first plane, a second portion 2112 in a second plane that is joined to the first portion 2110 at the bend 2108. The bend 2108 may have a bend angle A7, where the bend angle A7 may be from about 30° to about 100°, e.g., 90°. The guide opening 2104 may optionally comprise an insertion region 2114 that may be sized and shaped to accommodate a tissue-removal device therethrough. The insertion region 2114 may be co-planar with the first portion 2110, and may be wider than the first and second portions 2110, 2112. For example, the widest portion of the second portion 2112 may have a width W7, the widest portion of the first portion 2110 may have a width W8, and the widest portion of the insertion region 2114 may have a width W9, where the width W7 may be similar to the width W8, and the width W9 may be wider than both widths W7 and W8. The width W7 of the second portion may be from about 0.1 inch to about 0.3 inch, e.g., 0.25 inch, the width W8 of the first portion may be from about 0.1 inch to about 0.3 inch, e.g., 0.25 inch, and the width W9 of the insertion region 2114 may be from about 0.4 inch to about 0.6 inch, e.g., 0.5 inch. In some variations, the width W9 of the insertion region may be greater than the largest diameter of a distal portion of a tissue-removal device.

Figure 21C:
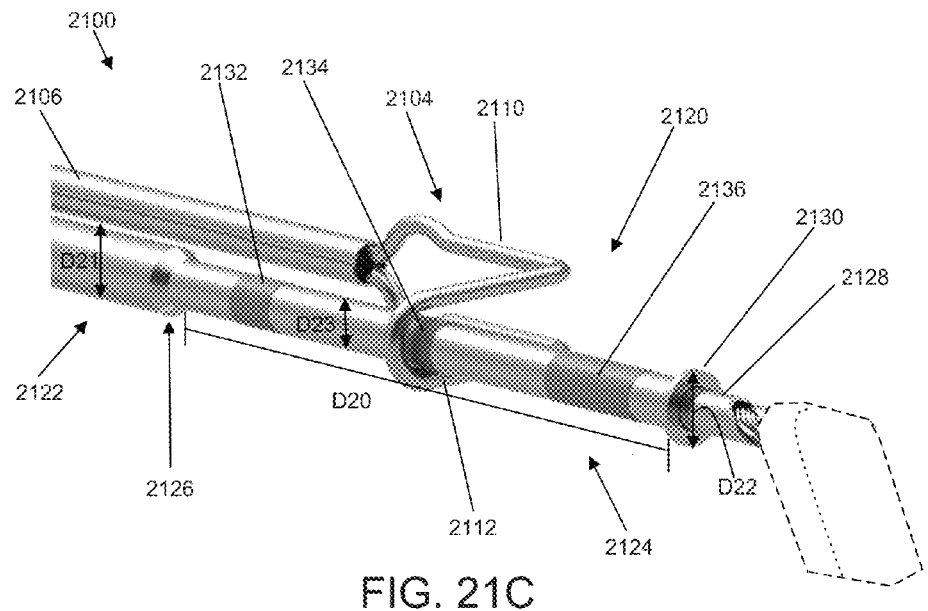

In some variations, the geometry of the guide opening 2104 in conjunction with the geometry of the distal portion of a tissue-removal device inserted in the guide opening may also restrict the axial movement of the tissue-removal device through the guide opening. For example, varying the widths W7, W8, and/or W9, as well as the width(s) of the distal portion of a tissue-removal device shaft, may control the axial movement of the device through different portions of the guide opening. For example, the various widths of the guide opening and the distal shaft of the tissue-removal device may constrain the depth to which the tissue-removal device may be inserted into a patient. As depicted in FIG. 21C, the distal portion of a tissue-removal device may have one or more features that interface with a travel limiter and/or access device to help advanced and/or position the tissue-removal assembly during a spinal procedure. For example, the distal portion of a shaft 2120 of a tissue-removal device may have a proximal portion 2122 that may be connected to a distal portion 2124 by a first shoulder 2126, and a shaft tip 2128 that may be distally connected to the distal portion 2124 by a second shoulder 2130. The diameter D21 of the proximal portion 2122 and the diameter D22 of the second shoulder 2130 may be larger than the diameter D23 of the distal portion 2124. The distance D20 between the first shoulder 2126 and the second shoulder 2130 may define a range of axial motion that the travel limiter or an access device may constrain the shaft to. In some variations, a travel limiter guide opening 2104 may be sized such that the width(s), e.g., W7 and W8, of the guide opening is greater than the diameter D23, but smaller than the diameters D21 and D22 of the first and second shoulders. Since the diameters of the first and second shoulders are greater than the width of the guide opening 2104, the shaft 2120 of the tissue-removal device may be axially translated along the narrowed distal portion 2124 between the first and second shoulders 2126 and 2130, but may not be axially translated past the first and second shoulders. Optionally, the distal portion 2124 of the shaft 2120 between the first shoulder 2126 and the second shoulder 2130 may comprise one or more length indicators that may indicate the distance that the shaft has been translated, e.g., insertion depth of the shaft during use. For example, the shaft 5202 may comprise a first marker 2132, a second marker 2134, and a third marker 2136 anywhere along the shaft length, e.g., the distal portion 2124. The markers may be equally spaced along the distal portion 2124, be equidistant from each other, or may be irregularly spaced. For example, the markers may be spaced 0.25 inch, 0.5 inch, 0.75 inch, 1 inch, etc. away from each other.

Figure 21D:
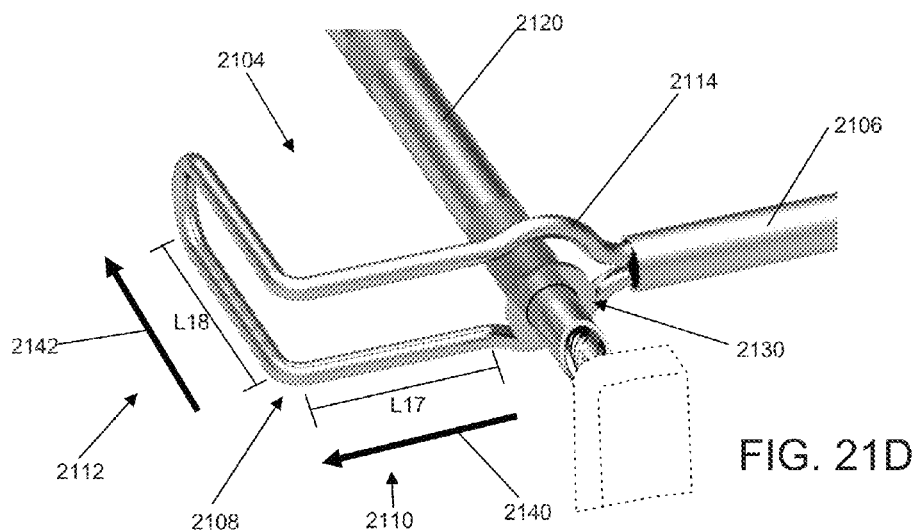

The shaft 2120 of the tissue-removal device may be engaged within the guide opening 2104 by inserting the shaft through the insertion region 2114, as illustrated in FIG. 21D. As described previously, the width W9 of the insertion region 2114 may be larger than the diameter of the shoulders of the shaft, e.g., the width W9 may be larger than the diameter D22 of the second shoulder 2130. Once inserted through the insertion region 2114, the shaft 2120 may be moved along the first portion 2110, e.g., in the direction of arrow 2140 towards the bend 2108. In this orientation, the shaft may be constrained to move a length L17 along the arrow 2140, where the length L17 may be from about 0.3 inch to about 0.8 inch, e.g., 0.4 inch. To traverse the bend 2108, the shaft 2120 may be axially twisted or rotated, for example, the shaft 2120 may be adjusted such that the longitudinal axis of the shaft is substantially parallel to the longitudinal axis of the elongate body 2106. In this orientation (depicted in FIG. 21C), the shaft 2120 may be moved along the second portion 2112, e.g., in the direction of arrow 2142, and the shaft may be constrained to move a length L18 along the arrow 2142, where the length L18 may be from about 0.25 inch to about 0.5 inch, e.g., 0.35 inch.

While the guide opening 2104 of the travel limiter 2100 has a single bend 2108, other variations of a guide opening may have a plurality of bends. In some variations, the plurality of bends may define a plurality of portions along which the tissue-removal device movement may be constrained. The different portions may be in a plurality of unique planes, or may be substantially co-planar. The guide opening may have rounded, tapered, and/or expanded regions, which may further guide and/or constrict the movement of a tissue-removal device inserted therethrough. For example, a looped guide opening may have two bends that define three portions. The three portions may be substantially co-planar, such that the movement of a shaft inserted therethrough is constrained only in that plane, by the boundaries of the guide opening. Alternatively, the three portions may occupy two or more unique planes, where the movement of a shaft in the guide opening may be constrained in multiple planes. The different planes of a guide opening may accommodate the geometry of the target tissue site, such that the tissue-removal device may be constrained in a fixed orientation regardless of the tissue geometry. In some variations, the first and third portion may occupy planes that are substantially parallel, such that a shaft may be inserted transversely through both the first and second portions. This may provide added stability as the tissue-removal device is used. The surface of the guide opening may be modified to increase or decrease the frictional forces between the shaft of the tissue-removal device and the guide opening, and in some variations, the surface may be coated with an anti-coagulant agent to reduce bleeding at the point of entry.

Another variation of a travel limiter may comprise an outer tube that is axially slidable relative to the impeller. The tube may have a flange from about 1 mm to about 5 mm from the distal end, which may help it to anchor onto the surface around the access hole such as the annulus of the disc. A proximal assembly may limit the travel of the tube to a specified distance of about 5 mm to 30 mm. Other variations of travel limiters are described below.

The orientation and position of the guide opening may be adjusted by a proximal handle 2102, one example of which is shown in FIG. 21A. The handle 2102 may be connected to the guide opening 2104 by the elongate body 2106, where the elongate body 2106 may have one or more angles to help a practitioner position the travel limiter 2100 during a spinal procedure. For example, the elongate body 2106 may have a first segment 2108 and a second segment 2109, where the first and second segments are separated by a first bend 2107. The first segment 2108 may have a length L15, where L15 may be from about 1 inch to about 2.5 inches, e.g., 1.5 inches. The second segment 2109 may have a length L16, where L16 may be from about 5 inches to about 8 inches, e.g., 6.25 inches. The first bend 2107 may have an angle A5, which may be from about 75° to about 100°, e.g., 90°. The first segment 2108 may also a second angle A6 with the handle 2102, where the angle A6 may be from about 75° to about 100°, e.g., 90°. Other variations of a travel limiter elongate body may have one or more pre-shaped bends or curves with various radii of curvature, e.g., rounded angles, helices, coils, quarter or half turns, etc., as appropriate for accommodating the anatomy of the patient, and the access path chosen by the practitioner.

Figure 21E:
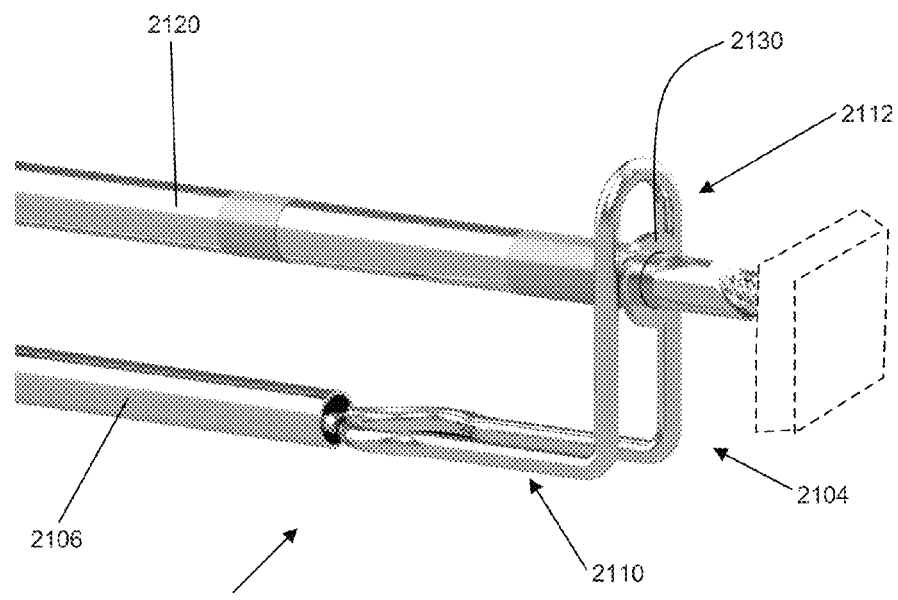
Figure 21F:
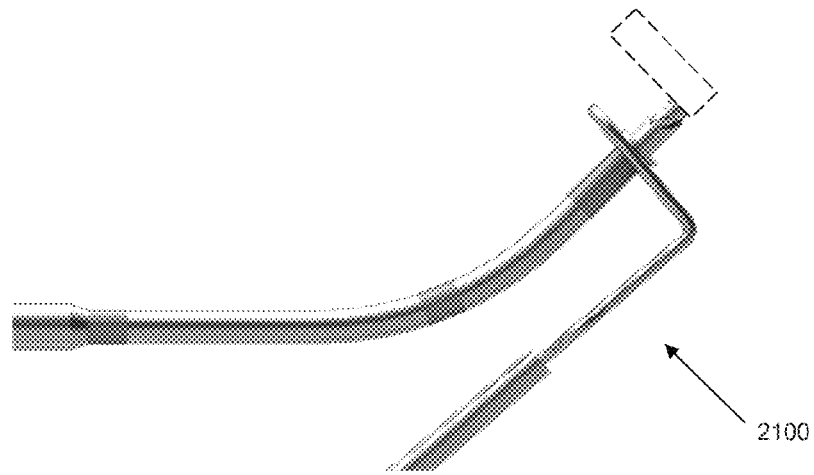

The travel limiter and the tissue-removal devices described above may be used in a surgical procedure, for example, to perform a discectomy in the course of an interbody fusion procedure. A practitioner may first test the tissue-removal device to ensure that it operates as desired, e.g., by powering the tissue-removal device on and off, expanding and collapsing the tissue removal assembly, etc. Once access is obtained to the target disc level, an annulotomy may be performed. About 1 cubic centimeter of saline may be injected into the middle of the disc. A tissue-removal device may be inserted through the guide opening of a travel limiter at the insertion region. For example, as shown in FIG. 21E, the tissue-removal device shaft 2120 may be inserted into the guide opening 2104 and moved to the distal part of the second portion 2112. FIG. 21F depicts how a tissue-removal device with a curved shaft may also be used with a travel limiter. The shaft 2120 may be pulled proximally so that the second shoulder 2130 is pressed against the guide opening 2104, which may limit further proximal movement. The tissue-removal device shaft 2120 and the travel limiter 2100 assembly may be advanced to the target disc. The travel limiter 2100 may be held stable against the outer annulus. The distal tip of the tissue-removal device may be positioned just inside the annulus. The tissue-removal device may be activated to rotate and may also be transitioned from a collapsed configuration to an expanded configuration. While the tissue-removal device is activated, the travel limiter may help to ensure that it is not removed from the patient during treatment. The tissue-removal device may be moved in small, expanding circular motions, which may gradually increase the size of the discectomy cavity and removed the target tissue. The quantity of tissue removed may be evaluated using Penfield or other metric. The tissue-removal device may be re-activated until the desired quantity of tissue has been removed. The tissue-removal device may be configured such that it should not be activated for more than 5 minutes to 10 minutes. Once a sufficient quantity of tissue has been removed, the tissue-removal device may be turned off and returned to a collapsed configuration. The tissue-removal device may then be withdrawn from the disc, and may be re-positioned at another disc level, or be withdrawn entirely. Devices for interbody fusion of vertebrae may be introduced as known by one of ordinary skill in the art.

Examples of procedures that may be used to access the spine are disclosed in U.S. Pat. No. 7,108,705, U.S. Pat. No. 4,573,448, U.S. Pat. No. 6,217,5009, and U.S. Pat. No. 7,273,468, which are hereby incorporated by reference in their entirety. The various embodiments of the tissue removal device disclosed herein may be used to perform a discectomy or nucleotomy, but may also be used to perform any of a variety of tissue removal procedures in the spine and outside of the spine.

It is to be understood that this invention is not limited to particular exemplary embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a blade" includes a plurality of such blades and reference to "the energy source" includes reference to one or more sources of energy and equivalents thereof known to those skilled in the art, and so forth.

The publications discussed herein are provided solely for their disclosure. Nothing herein is to be construed as an admission that the present invention is not entitled to antedate such publication by virtue of prior invention. Further, the dates of publication provided, if any, may be different from the actual publication dates which may need to be independently confirmed.

What is claimed as new and desired to be protected by Letters Patent of the United States is:

1. A discectomy system, comprising:
   a proximal handheld housing including a motor;
   an outer shaft attached to the handheld housing;
   an inner shaft located within the outer shaft and including
      a proximal section coupled to the motor;
   a tissue removal assembly comprising a cutting block element, including:
      an inner section attached to a distal section of the inner shaft;
      an outer section spaced from the inner shaft;
      a cutting structure comprising a leading edge, a trailing surface and a trailing edge, wherein at least a portion of the trailing edge being located radially inward relative to the leading edge; and a flow control structure comprising a leading edge, a trailing edge, and a flow control surface located between the leading edge and trailing edge of the flow control structure, the flow control surface having a length greater than a length of a radial line extending from the inner shaft to the leading edge of the cutting structure.

2. The discectomy system of claim 1, wherein an average diameter of the outer shaft is less than about 3 mm.

3. The discectomy system of claim 1, wherein an average diameter of the inner shaft is less than about 2 mm.

4. The discectomy system of claim 1, wherein the leading edge of the cutting structure has a linear configuration.

5. The discectomy system of claim 1, wherein the trailing surface of the cutting structure has a planar configuration.

6. The discectomy system of claim 1, wherein the leading edge of the flow control structure has a generally transverse orientation with respect to the inner shaft.

7. The discectomy system of claim 1, wherein the leading edge of the flow control structure is transverse to the leading edge of the cutting structure.

8. The discectomy system of claim 1, wherein the flow control surface of the flow control structure has a planar configuration.

9. The discectomy system of claim 1, wherein the flow control structure further comprises a distal edge and a proximal edge.

10. The discectomy system of claim 1, wherein the tissue removal assembly is asymmetrically configured with respect to the inner shaft.

* * * * *